United States Patent
Madigan et al.

(10) Patent No.: US 9,339,433 B2
(45) Date of Patent: May 17, 2016

(54) METHODS OF DIAGNOSING AND TREATING NEONATAL REVERSION TO FETAL CONSCIOUSNESS

(71) Applicant: The Regents of the University of California, Oakland, CA (US)

(72) Inventors: John E. Madigan, Woodland, CA (US); Monica R. Aleman, West Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/162,753

(22) Filed: Jan. 24, 2014

(65) Prior Publication Data

US 2014/0213563 A1 Jul. 31, 2014

Related U.S. Application Data

(60) Provisional application No. 61/756,957, filed on Jan. 25, 2013.

(51) Int. Cl.
| | |
|---|---|
| G01N 33/53 | (2006.01) |
| G01N 31/00 | (2006.01) |
| A61H 9/00 | (2006.01) |
| G01N 33/74 | (2006.01) |
| A61D 99/00 | (2006.01) |
| G01N 33/68 | (2006.01) |

(52) U.S. Cl.
CPC ............... *A61H 9/005* (2013.01); *A61D 99/00* (2013.01); *G01N 33/6893* (2013.01); *G01N 33/743* (2013.01); *A61H 2203/03* (2013.01); *G01N 2800/38* (2013.01)

(58) Field of Classification Search
CPC ..................... A61K 31/00; G01N 2333/91194; G01N 2500/00; C12Q 1/48
See application file for complete search history.

(56) References Cited

PUBLICATIONS

Tascilar et al. (Annals of Oncology 10,Suppl. 4:S107-S110, 1999).*
Tockman et al. (Cancer Research 52:2711s-2718s, 1992).*
Diesch, T.J. et al., "Birth transitions: Pathophysiology, the onset of consciousness and possible implications for neonatal maladjustment syndrome in the foal," *Equine Veterinary Journal* 45 (2013) 656-660.
https://vimeo.com/68410389.
https://vimeo.com/68095552.
https://vimeo.com/62660440.
https://vimeo.com/62660441.
https://vimeo.com/62660442.
https://www.youtube.com/watch?v=mKbwOv7eQKc.
Aleman, M. et al., "Abnormal plasma neuroactive progestogen derivatives in ill, neonatal foals presented to the neonatal intensive care unit," *Equine Vet J*, Nov. 2013;45(6):661-5, epublished Apr. 22, 2013.
Blunden, Tony, "Fading puppies—reality or myth?" *In Practice*, Jun. 2012, vol. 34, 314-321.
Dickey, E.J. et al., "Hypoxic Ischemic Encephalopathy—what can we learn from humans?" *Review J Vet Intern Med* 2011;25:1231-1240.
Dwyer, C.M. et al., "Invited review: Improving neonatal survival in small ruminants: science into practice," *Animal*, © The Animal Consortium 2015, May 2015, pp. 1-11.
Freshman, Joni L., "Fading puppy and kitten syndrome: Do you know the signs?" *Veterinary Medicine*, Nov. 2005, 807-808.
Hess-Dudan, et al. 1996, "Neonatal maladjustment syndrome and other neurological signs in the newborn foal: Part 1," *Equine Veterinary Education* 8(1):24-32.
Hess-Dudan, et al. 1996, "Neonatal maladjustment syndrome and other neurological signs in the newborn foal: Part 2," *Equine Veterinary Education* 8(2):79-83.
Kelly, Tara, "Jamie Ogg, baby pronounced dead then revived by mother's touch, celebrates second birthday this month," *The Huffington Post*, posted Mar. 9, 2012., downloaded from http://www.huffingtonpost.com/2012/03/09/jamie-ogg-back-to-life_n_1333297.html.
Lagercrantz, Hugo, "The birth of consciousness," *Early Human Development* 85 (2009) 557-558.
Lawn, Joy E., et al. 2010, "'Kangaroo mother care' to prevent neonatal deaths due to preterm birth complications," *International Journal of Epidemiology* 2010;39:i144-i154.
Madigan, et al. 2012, "Allopregnanolone infusion induced neurobehavioural alterations in a neonatal foal: Is this a clue to the pathogenesis of neonatal maladjustment syndrome?" *Equine Veterinary Journal* 44, Suppl. 41 (2012) 109-112.
Majewska, et al. 2014, "Marked elevation of adrenal steroids, especially androgens, in saliva of prepubertal autistic children," *Eur Child Adolesc Psychiatry* (2014) 23:485-498.
Meade, Clare, "Fading syndrome in kittens," *In Practice*, Jun. 2014, vol. 36, 266-276.
Mee, John F., "Managing the calf at calving time," *The AABP Proceedings*, vol. 41, Sep. 2008, 46-53.
Mellor, D.J. et al., "Animal welfare implications of neonatal mortality and morbidity in farm animals," *The Veterinary Journal* 168 (2004) 118-133, Aug. 13, 2003.
Mellor, David J., "Galloping colts, fetal feelings, and reassuring regulations: putting animal-welfare science into practice," *Journal of Veterinary Medical Education (JVME)* 37(1) 2010 AAVMC, 94-100.
Mellor, D.J. et al., "Responsiveness, behavioural arousal and awareness in fetal and newborn lambs: experimental, practical and therapeutic implications," *New Zealand Veterinary Journal* 51(1), 2-13, 2003.
Mercer, Judith S. et al., "Evidence-based practices for the fetal to newborn transition," *Journal of Midwifery & Women's Health*, vol. 52, No. 3, May/Jun. 2007, 262-272.
Rossdale, et al. 1995, "A Retrospective Study of Increased Plasma Progestagen Concentrations in Compromised Neonatal Foals," *Reprod. Fertil. Dev.* 7:567-575.
Toth, et al. 2012, "Evaluation of squeeze-induced somnolence in neonatal foals." *Am J Vet Res.* 73(12):1881-1889.

* cited by examiner

*Primary Examiner* — Lisa Cook
(74) *Attorney, Agent, or Firm* — Weaver Austin Villeneuve & Sampson LLP

(57) ABSTRACT

This invention provides methods of diagnosing and treating syndromes of reversion to fetal consciousness in a neonate.

38 Claims, 6 Drawing Sheets

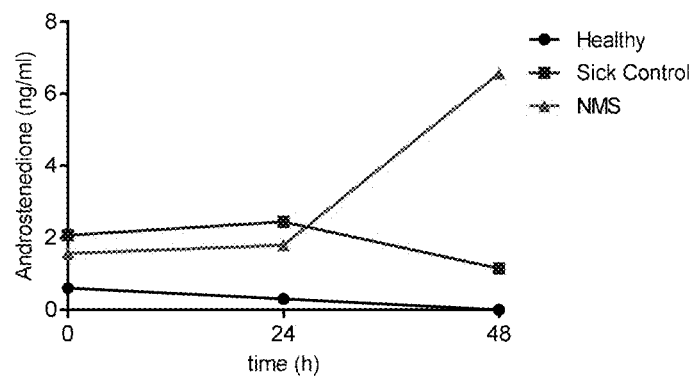
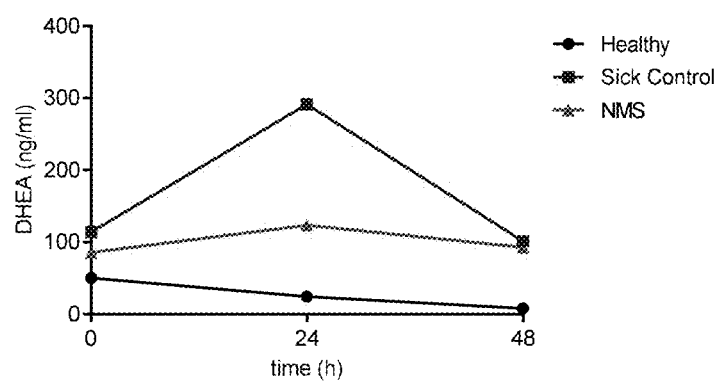
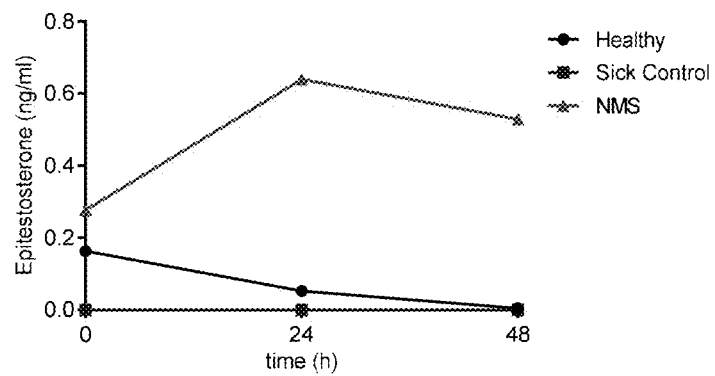
*Fig. 2A-C*

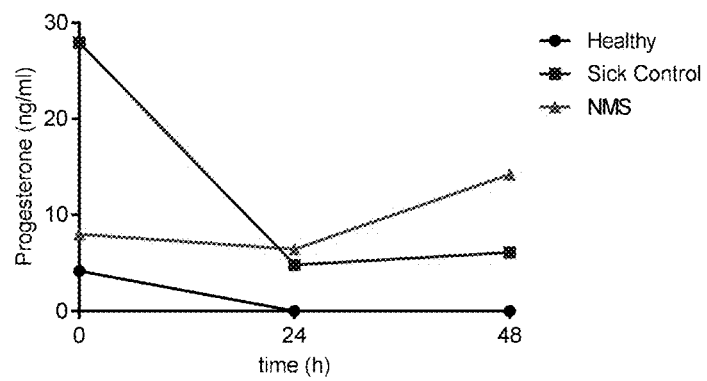
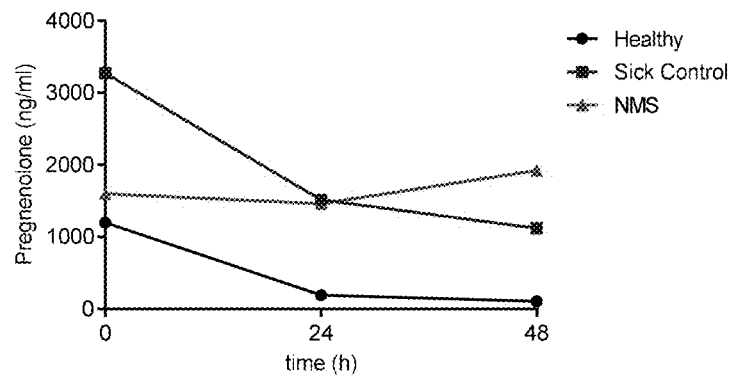
*Fig. 2D-E*

METHODS OF DIAGNOSING AND TREATING NEONATAL REVERSION TO FETAL CONSCIOUSNESS

CROSS-REFERENCE TO RELATED APPLICATIONS

This application claims the benefit under 35 U.S.C. §119 (e) of U.S. Provisional Application No. 61/756,957, filed on Jan. 25, 2013, which is hereby incorporated herein by reference in its entirety for all purposes.

FIELD

The present invention relates to methods of diagnosing and treating syndromes of reversion to fetal consciousness in a neonate.

BACKGROUND

Neonatal maladjustment syndrome (NMS) is a common disorder of neonatal foals that manifests within the first 72 h of life (Bernard, et al (1995) In: *Proceedings,* 41st American Association of Equine Practitioners, Lexington, Ky. pp 222-224; Rossdale and Leadon, (1975) *J Reprod Fertil* 23, 658-661). The proposed mechanisms include hypoxic and ischaemic events prior to, during and shortly after parturition (Palmer and Rossdale, (1976) *Res Vet Sci* 20, 267-275). Affected foals exhibit neurological dysfunction such as seizures and altered states of consciousness, behaviour and response to stimuli (Bernard et al. 1995, supra; Ringger, et al. (2011) *J Vet Intern Med* 25, 132-137). However, hypoxic and ischaemic injury is not always identified upon histopathological evaluation, and long-term neurological deficits have been reportedly rare. Fetal corticosteroids, through activation of the hypothalamo-pituitary-adrenocortical (HPA) axis, contribute to the maturation of many organs and regulate the transition between intra- and extrauterine life (Rossdale, (2004) In: *Proceedings,* 51st American Association of Equine Practitioners, Denver, Colo. pp 75-126). Rossdale, et al., ((1995) *Reprod Fertil Dev* 7, 567-575) reported increased concentrations of progestagens in neonatal foals that rapidly decrease over the following 48 h after birth (Houghton, et al., (1991) *J Reprod Fert Suppl* 44, 609-617; Rossdale 2004, supra). Foals with NMS have been reported to have persistently increased concentrations of plasma progestagens (Houghton et al. 1991, supra; Rossdale et al. 1995, supra; Rossdale 2004, supra). Concentrations of several plasma steroids including progestagens (progesterone and pregnenolone) and androgens (epitestosterone and androstenedione) were found to be significantly increased in foals with NMS compared with healthy foals (Aleman et al, (2013) *Equine Veterinary Journal*). Certain steroidal compounds called neurosteroids, predominantly 5-α reduced pregnanes, can cross the blood-brain barrier and have neuromodulatory effects (Mellon and Griffin (2002) *Trends Endocrinol Metab* 13, 35-43; Naert, et al. (2007) *Psychoneuroendocrinology* 32, 1062-1078). It is proposed that in a subset of foals the signs of NMS may not be the result of hypoxia, and that these neurosteroids may play a role in the aetiology and clinical manifestations of foals with NMS.

NMS has been referred to as hypoxic-ischemic encephalopathy, perinatal asphyxia, neonatal encephalopathy, and dummy foal syndrome (Drummond (1988) *Equine Vet J* 5, 41-43; Vaala, (1994) *Vet Clin N Am Equine Pract* 10, 187-218). The proposed pathogenesis is the result of hypoxia and ischemia of the brain which occurs shortly before, during or after parturition leading to neuronal cellular energy failure and death (Drummond (1988) *Equine Vet J* 5, 41-43; Rossdale (1972) *Equine Vet J* 4, 117-128; Ringger, et al., (2011) *J Vet Intern Med* 25, 132-137). Clinical signs are consistent with brain hypoxia and include alterations in the state of consciousness from mild obtundation to stuporous to comatose; abnormal behaviour such as lack of affinity for the mare, not nursing, vocalization, and wandering; blindness; and paroxysmal activity such as paddling and seizures (Palmer and Rossdale (1976) *Res Vet Sci* 20, 267-275). Histopathological evidence of cerebral hemorrhage and hypoxia has been detected in some severely affected foals (Palmer and Rossdale (1976), supra). However, many foals do not have histological evidence of hypoxia, edema or hemorrhage (Bernard, et al., In: *Proceedings,* 41st American Association of Equine Practitioners, Lexington, Ky. pp 222-224). Furthermore, many foals have a normal birth and recover quickly and fully from the condition. This is in contrast to infants and newborn rats with asphyxia in which a significantly longer recovery time is needed and long-term neurological deficits are often manifest (Kiss, et al., (2009) *Brian Res* 1255, 42-50; van Handel, et al., (2007) *Eur J Pediatr* 166, 645-654). The fast recovery with no apparent long-term deficits and lack of evidence of hypoxia or ischemia in affected neonatal foals suggest that the syndrome may not be exclusively the result of hypoxia.

Neonatal foals have high concentrations of pregnanes at birth which decrease rapidly over the first 48 hours of life (Houghton, et al., (1991) *J Reprod Fertil* 44, 609-617). Elevated concentrations of plasma pregnanes and a correlation between decreasing levels of pregnanes and clinical recovery have been reported (Rossdale, et al., (1995) *Reprod Fertil Dev* 7, 567-575). Certain steroidal compounds, predominantly 5-α reduced pregnanes, appear to have important neuromodulatory roles (Baulieu, (1998) *Psychoneuroendocrinology* 23, 963-987; Mellon and Griffin (2002) *Trends Endocrinol Metab* 13, 35-43; Robel and Baulieu, (1994) *Trends Endocrinol Metab* 5, 1-8). These steroids are synthesized de novo in glial cells from cholesterol or blood-borne steroid precursors (Robel, et al., (1994) *Trends Endocrinol Metab* 5:1-8) and are potent allosteric modulators of the $GABA_A$ receptor; low concentrations cause weak enhancement of GABA activity and high concentrations cause complete non-competitive inhibition (Baulieu (1998) *Psychoneuroendocrinology* 23, 963-987). Infusion of certain 5α-reduced pregnanes into rats and mice (Naert, et al., (2007) *Psychoneuroendocrinology* 32, 1062-1078; Zhu, et al., (2001) *Br J Anaesth* 86, 403-412) and neonatal foals (Madigan, et al., (2012) *Equine Vet J* 44 S41 109-112.) leads to anaesthesia or marked behavioural effects suggesting that these pregnanes cross the blood brain barrier and exert neuromodulatory effects.

SUMMARY

In one aspect, provided are methods of diagnosing a syndrome of reversion to fetal consciousness in a neonate mammal. In some embodiments, the methods comprise:

a) measuring or assaying the levels of one or more pregnanes in a biological sample from the neonate mammal and;

b) diagnosing the neonate mammal as suffering reversion to fetal consciousness when elevated or detectable levels of the one or more pregnanes are measured.

In a further aspect, provided are methods of diagnosing a syndrome of reversion to fetal consciousness in a neonate mammal. In some embodiments, the methods comprise:

a) receiving a report providing the levels of one or more pregnanes in a biological sample from the neonate mammal and;

b) diagnosing the neonate mammal as suffering reversion to fetal consciousness when elevated or detectable levels of the one or more pregnanes are measured.

In another aspect, provided are methods of diagnosing a syndrome of reversion to fetal consciousness in a neonate mammal. In some embodiments, the methods comprise:

a) measuring or assaying a level of one or more neurosteroids in a biological sample from the neonate mammal and;

b) diagnosing the neonate mammal as suffering reversion to fetal consciousness when the level of the one or more neurosteroids is elevated above a threshold level.

In a further aspect, provided are methods of diagnosing a syndrome of reversion to fetal consciousness in a neonate mammal. In some embodiments, the methods comprise:

a) receiving a report providing a level of one or more neurosteroids in a biological sample from the neonate mammal and;

b) diagnosing the neonate mammal as suffering reversion to fetal consciousness when the level of the one or more neurosteroids is elevated above a threshold level.

In a further aspect, provided are methods of detecting an indicator of reversion to fetal consciousness in a neonatal mammalian subject, the method comprising assaying a blood sample from the subject for a panel of neurosteroids, wherein the presence of one or more of the neurosteroids at a detectable level or a level above a predetermined threshold level indicates the presence reversion to fetal consciousness in the subject.

With respect to embodiments of the diagnostic methods, in some embodiments, the neonate mammal is selected from the group consisting of a human, a non-human primate, Equidae, Bovidae, Cervidae, Suidae, Canidae, Felidae, Rodentia, Lagomorpha, Camelidae, Ursidae, Procyonidae, Mustelidae, Elephantidae. In some embodiments, the neonate mammal is an equine. In some embodiments, the neonate mammal is exhibiting symptoms of reversion to fetal consciousness (e.g., diminished mentation, inability and/or unwillingness to breathe properly using lungs, inability and/or unwillingness to nurse, inability to stand and/or unstable gait).

In varying embodiments, the one or more neurosteroids measured or assayed comprise one or more pregnanes, one or more androgens and/or one or more estrogens. In varying embodiments, the panel of neurosteroids assayed or measured comprises one or more or all pregnanes selected from the group consisting of allopregnanolone (3α-hydroxy-5α-pregnan-20-one or 3α,5α-tetrahydroprogesterone; also abbreviated as THP or THPROG), allopregnanolone sulfate, 5α-dihydroprogesterone (DHP), 17-hydroxypregnenolone, 17-hydroxyprogesterone, pregnanediol, pregnenolone, pregnenolone sulfate and progesterone; one or more or all androgens/estrogens selected from the group consisting of androstenedione, 1,4-androstadiene-3, 17-1, boldenone, boldenone sulfate, dehydroepiandrosterone (DHEA), 5-α dihydroandrolone, 5-α dihydrotestosterone, 5-β dihydrotestosterone, epinandrolone, epistestosterone, 17-α estradiol, 17-β estradiol, 17-β estradiol sulfate, 5-α-estran-3-β-17 diol, estrone, estrone sulfate, 6-α-hydroxyandrostenedione, nandrolone, nandrolone glucuronide, nandrolone sulfate, 19-norandrostenedione, 19-nor-androsterone, 19-norepiandrosterone, testosterone, testosterone glucuronide and testosterone sulfate. Additionally, one or more or all compounds selected from the group consisting of adrenocorticotropic hormone (ACTH), adenosine, cortisol and oxytocin may be assayed or measured. In varying embodiments, the pregnanes measured comprise neurosteroidal activity. In varying embodiments, the pregnanes measured comprise adrenally-derived pregnanes. In varying embodiments, the level of one or more, e.g., 1, 2, 3, 4, 5, 6, 7, 8 or 9, pregnanes selected from the group consisting of allopregnanolone (3α-hydroxy-5α-pregnan-20-one or 3α,5α-tetrahydroprogesterone; also abbreviated as THP or THPROG), allopregnanolone sulfate, 5α-dihydroprogesterone (DHP), 17-hydroxypregnenolone, 17-hydroxyprogesterone, pregnanediol, pregnenolone, pregnenolone sulfate and progesterone is measured or assayed. In some embodiments, one or more, e.g., one, two, three or four pregnanes, selected from the group consisting of progesterone, pregnenolone, 17OH progesterone and pregnanediol are measured. In some embodiments, one or more pregnanes selected from the group consisting of progesterone and pregnenolone are measured. In varying embodiments, the levels of pregnenolone in the biological sample are measured. The levels of the one or more pregnanes in the biological sample can be compared with a predetermined threshold level. In some embodiments, the level of one or more, e.g., 1, 2, 3, 4, 5, 6, 7, 8, 9, 10, 11, 12, 13, 14, 15, 16, 17, 18, 19, 20, 21, 22, 23, 24, 25, 26 or 27, androgens/estrogens selected from the group consisting of androstenedione, 1,4-androstadiene-3, 17-1, boldenone, boldenone sulfate, dehydroepiandrosterone (DHEA), 5-α dihydroandrolone, 5-α dihydrotestosterone, 5-β dihydrotestosterone, epinandrolone, epistestosterone, 17-α estradiol, 17-β estradiol, 17-β estradiol sulfate, 5-α-estran-3-β-17 diol, estrone, estrone sulfate, 6-α-hydroxyandrostenedione, nandrolone, nandrolone glucuronide, nandrolone sulfate, 19-norandrostenedione, 19-norandrosterone, 19-norepiandrosterone, testosterone, testosterone glucuronide and testosterone sulfate is assayed or measured. In varying embodiments, the level of one or more compounds selected from the group consisting of adrenocorticotropic hormone (ACTH), adenosine, cortisol and oxytocin is additionally assayed or measured. Levels of the one or more neurosteroids, e.g., the one or more pregnanes and/or the one or more androgens/estrogens above the predetermined threshold level indicate and/or are associated with a positive diagnosis of reversion to fetal consciousness. In varying embodiments, the predetermined threshold level for the neurosteroids selected from allopregnanolone (3α-hydroxy-5α-pregnan-20-one or 3α,5α-tetrahydroprogesterone; also abbreviated as THP or THPROG), allopregnanolone sulfate, 5α-dihydroprogesterone (DHP), 17-hydroxypregnenolone, 17-hydroxyprogesterone, pregnanediol, pregnenolone sulfate, 1,4-androstadiene-3, 17-1, boldenone, boldenone sulfate, 5-α dihydroandrolone, 5-α dihydrotestosterone, 5-β dihydrotestosterone, epinandrolone, 17-α estradiol, 17-β estradiol, 17-β estradiol sulfate, 5-α-estran-3-β-17 diol, estrone, estrone sulfate, 6-α-hydroxyandrostenedione, nandrolone, nandrolone glucuronide, nandrolone sulfate, 19-norandrostenedione, 19-nor-androsterone, 19-norepiandrosterone, testosterone, testosterone glucuronide and testosterone sulfate, adrenocorticotropic hormone (ACTH), adenosine, cortisol and oxytocin is above 0.0001 ng/mL or any detectable level. In varying embodiments, the predetermined threshold level for androsterone, DHEA, epitestosterone, progesterone and pregnenolone at ages O-few hours of age, 24 h, and 48 h old are as shown in Table 1. In varying embodiments, the threshold value for ACTH is 53 ng/mL), the threshold value for cortisol is 16 ng/mL, the threshold value for adenosine is 0.3 ng/mL), and the threshold value for oxytocin is 1.1 ng/mL.

TABLE 1

| Steroid (ng/mL) | 0 h | 24 h | 48 h |
| --- | --- | --- | --- |
| androstenedione | 0.6 | 0.3 | 0.0001 (any detectable level) |
| DHEA | 50 | 25 | 8 |
| epitestosterone | 0.2 | 0.05 | 0.004 |
| progesterone | 4 | 0.0001 (any detectable level) | 0.0001 (any detectable level) |
| pregnenolone | 1200 | 193 | 104 |

In varying embodiments, the elevated pregnenolone levels are above about 6000 ng/ml under 24 hours post birth, above about 550 ng/ml at 24-28 hours post birth and/or above about 315 ng/ml at or after 48 hours post birth. In varying embodiments, the elevated pregnenolone levels are above about 12,900 ng/ml under 24 hours post birth, above about 3470 ng/ml at 24-28 hours post birth and/or above about 3420 ng/ml at or after 48 hours post birth. In varying embodiments, the elevated progesterone levels are above about 10.5 ng/ml under 24 hours post birth, above about 0.8 ng/ml at 24-28 hours post birth and/or above about 0.1 ng/ml at or after 48 hours post birth. In varying embodiments, the elevated progesterone levels are above about 9.7 ng/ml at 24-28 hours post birth and/or above about 14.3 ng/ml at or after 48 hours post birth.

In varying embodiments, the diagnostic methods further comprise measuring the level of one or more androgens/estrogens (in addition to the level of one or more pregnanes) in the biological sample. In some embodiments, the one or more androgens are selected from the group consisting of androstenedione, dehydroepiandrosterone (DHEA), DHEA-sulphate and epitestosterone are measured. In some embodiments, the level of one or more, e.g., 1, 2, 3, 4, 5, 6, 7, 8, 9, 10, 11, 12, 13, 14, 15, 16, 17, 18, 19, 20, 21, 22, 23, 24, 25, 26 or 27, androgens/estrogens selected from the group consisting of androstenedione, 1,4-androstadiene-3, 17-1, boldenone, boldenone sulfate, dehydroepiandrosterone (DHEA), 5-α dihydroandrolone, 5-α dihydrotestosterone, 5-β dihydrotestosterone, epinandrolone, epistestosterone, 17-α estradiol, 17-β estradiol, 17-β estradiol sulfate, 5-α-estran-3-β-17 diol, estrone, estrone sulfate, 6-α-hydroxyandrostenedione, nandrolone, nandrolone glucuronide, nandrolone sulfate, 19-norandrostenedione, 19-nor-androsterone, 19-norepiandrosterone, testosterone, testosterone glucuronide and testosterone sulfate is assayed or measured.

In varying embodiments, the biological sample is a fluid sample, e.g., selected from the group consisting of blood, serum, plasma, urine and saliva. In varying embodiments, the neonate is less than 120 hours post birth, e.g., less than 96, 84, 72, 60, 48, 36, 24, 12, 9, 6, 3, 2, 1 hours post birth. In varying embodiments, the neurosteroid (e.g., pregnane) levels are measured at two or more time points, e.g., two, three, four, five or more time points. A diagnosis of reversion to fetal consciousness is indicated when the levels of neurosteroids (e.g., pregnanes) remain elevated, increase or do not decrease at subsequent time points.

In varying embodiments, the diagnostic methods further comprise, upon measuring elevated neurosteroid (e.g., pregnane) levels and positively diagnosing the neonate mammal as suffering reversion to fetal consciousness, administering to the neonate an effective amount of a 5α reductase inhibitor. In some embodiments, the 5α reductase inhibitor is selected from the group consisting of alfatradiol, dutasteride, finasteride, bexlosteride, epristeride, izonsteride, lapisteride, turosteride, and analogs, salts and mixtures thereof. In some embodiments, the 5α reductase inhibitor is dutasteride.

In varying embodiments, the diagnostic methods further comprise, upon measuring elevated neurosteroid (e.g., pregnane) levels and positively diagnosing the neonate mammal as suffering reversion to fetal consciousness, subjecting the neonate to squeezing or hugging along the mid-thorax. In varying embodiments, the applied pressure of the squeezing is maintained for at least 10 minutes, e.g., at least 15, 20, 25, 30, 35, 40, 45, 50, 55 or 60 minutes. In varying embodiments, the squeezing or hugging of the neonate applies substantially uniform pressure along the mid-thorax of the neonate. In varying embodiments, the squeezing or hugging of the neonate comprises skin-to-skin contact.

In a further aspect, methods of preventing, reversing and/or mitigating a syndrome of reversion to fetal consciousness in a neonate mammal. In some embodiments, the methods comprise administering to the neonate an effective amount of a 5α reductase inhibitor. In varying embodiments, the 5α reductase inhibitor is selected from the group consisting of alfatradiol, dutasteride, finasteride, bexlosteride, epristeride, izonsteride, lapisteride, turosteride, and analogs, salts and mixtures thereof. In varying embodiments, the 5α reductase inhibitor is administered to the neonate less than 120 hours post birth, e.g., less than 96, 84, 72, 60, 48, 36, 24, 12, 9, 6, 3, 2, 1 hours post birth.

In another aspect, methods of preventing, reversing and/or mitigating a syndrome of reversion to fetal consciousness in a neonate mammal. In some embodiments, the methods comprise subjecting the neonate to squeezing or hugging along the mid-thorax. In varying embodiments, the applied pressure of the squeezing is maintained for at least 10 minutes, e.g., at least 15, 20, 25, 30, 35, 40, 45, 50, 55 or 60 minutes. In varying embodiments, the squeezing or hugging of the neonate applies substantially uniform pressure along the mid-thorax of the neonate. In varying embodiments, the squeezing or hugging of the neonate comprises skin-to-skin contact.

With respect to embodiments of the methods for preventing, reversing and/or mitigating a syndrome of reversion to fetal consciousness in a neonate mammal, in varying embodiments, the neonate is less than 120 hours post birth, e.g., less than 96, 84, 72, 60, 48, 36, 24, 12, 9, 6, 3, 2, 1 hours post birth. In varying embodiments, the neonate mammal has elevated levels of neurosteroids (e.g., pregnanes) in a fluid biological sample, e.g., in a blood, serum, plasma, urine and/or saliva sample. In some embodiments, one or more, e.g., one, two, three or four pregnanes selected from the group consisting of progesterone, pregnenolone, 17OH progesterone and pregnanediol are elevated. In some embodiments, one or both pregnanes selected from the group consisting of progesterone and pregnenolone are elevated. In some embodiments, pregnenolone is elevated. The levels of the one or more neurosteroids (e.g., pregnanes) in the biological sample can be compared with a predetermined threshold level.

In varying embodiments, the elevated pregnenolone levels are above about 6000 ng/ml under 24 hours post birth, above about 550 ng/ml at 24-28 hours post birth and/or above about 315 ng/ml at or after 48 hours post birth. In varying embodiments, the elevated pregnenolone levels are above about 12,900 ng/ml under 24 hours post birth, above about 3470 ng/ml at 24-28 hours post birth and/or above about 3420 ng/ml at or after 48 hours post birth. In varying embodiments, the elevated progesterone levels are above about 10.5 ng/ml under 24 hours post birth, above about 0.8 ng/ml at 24-28 hours post birth and/or above about 0.1 ng/ml at or after 48 hours post birth. In varying embodiments, the elevated progesterone levels are above about 9.7 ng/ml at 24-28 hours post birth and/or above about 14.3 ng/ml at or after 48 hours post birth. In varying embodiments, the levels of one or more androgens in the biological sample are elevated. In some embodiments, the one or more elevated androgens are selected from the group consisting of androstenedione, dehydroepiandrosterone (DHEA), DHEA-sulphate and epitestosterone. In some embodiments, the neonate mammal is selected from the group consisting of a human, a non-human primate, Equidae, Bovidae, Cervidae, Suidae, Canidae, Felidae, Rodentia, Lagomorpha, Camelidae, Ursidae, Procyonidae, Mustelidae, Elephantidae. In some embodiments, the neonate mammal is an equine.

In a further aspect, an inflatable cuff for squeezing and/or hugging the mid-thorax of a neonate mammal is provided. In some embodiments, the inflatable cuff comprises a pneumatic inflating sleeve of sufficient circumference to encircle the mid-thorax of a neonate mammal. In some embodiments, the pneumatic inflating sleeve is of a sufficient circumference to encircle the mid-thorax of a neonate from a species selected from the group consisting of human, non-human primate, Equidae, Bovidae, Cervidae, Suidae, Canidae, Felidae, Rodentia, Lagomorpha, Camelidae, Ursidae, Procyonidae, Mustelidae, Elephantidae. In some embodiments, the neonate mammal is an equine. In some embodiments, the pneumatic inflating sleeve is of a sufficient circumference to encircle the mid-thorax of an equine neonate. In some embodiments, the sleeve of the inflated cuff applies substantially even pressure along the length of the mid-throrax encircled by the sleeve. In some embodiments, the cuff further comprises straps for stably positioning the cuff around the mid-thorax. In some embodiments, the straps of the cuff are configured to encircle the neck of the mammal. In some embodiments, the cuff is in fluid communication with a foot pump or motorized pump capable of and suitable for inflating the cuff. In varying embodiments, the device comprises first and second inflatable cuffs.

DEFINITIONS

The term "reversion to fetal consciousness" refers to a syndrome occurring in a mammalian neonate within the first 72 hours of life manifesting clinical symptoms consistent with brain hypoxia including without limitation alterations in the state of consciousness from mild obtundation to stuporous to comatose; abnormal behavior such as lack of affinity for the mother, not nursing, blindness, vocalization, wandering and paroxysmal activity such as paddling and seizures.

The term "neonatal maladjustment syndrome (NMS)" refers to a condition affecting equine foals within the first 72 hours of life. Clinical signs are consistent with brain hypoxia and include without limitation alterations in the state of consciousness from mild obtundation to stuporous to comatose; abnormal behavior including lack of affinity for the mare, not nursing, vocalization, and wandering; blindness; and paroxysmal activity such as paddling and seizures. NMS is described and reviewed in, e.g., Hess-Dudan, et al., *Equine Vet Educ* (1996) 8(1):24-32 and Hess-Dudan, et al., *Equine Vet Educ* (1996) 8(2):79-83.

The terms "neurosteroid" and "neuroactive steroid" interchangeably refer to steroid compounds having the capability to alter neuronal excitability through interaction with neurotransmitter-gated ion channels. Illustrative neurosteroids include without limitation allopregnanolone, dehydroepiandrosterone, dehydroepiandrosterone sulfate, 5α-dihydroprogesterone, pregnenolone, progesterone and tetrahydrodeoxycorticosterone.

The term "pregnane" refers to in vivo steroid compounds stemming or derived from 5α-pregnane (a.k.a., allopregnane) and 5β-pregnane (17β-ethyletiocholane). Structurally, pregnanes have a 21 carbon nucleus and a core ring structure comprised of cyclopentanoperhydrophenanthrene. Functionally, many pregnanes have neurosteroidal activity (e.g., alter neuronal excitability through interaction with neurotransmitter-gated ion channels). Illustrative pregnanes measured in the present methods include without limitation, e.g., progesterone (pregn-4-ene-3,20-dione, CAS number 57-83-0), pregnenolone (β-hydroxypregn-5-en-20-one; CAS number 145-13-1), 17OH progesterone (17-Hydroxypregn-4-ene-3,20-dione; CAS number 68-96-2) and pregnanediol (5β-pregnane-3α,20α-diol; CAS number 80-92-2).

The term "threshold level" refers to representative or predetermined levels of one or more measured compounds (e.g., neurosteroid, pregnane, androgen) in a biological sample of a neonate. The threshold level can represent compound levels detected in a sample from a normal control or a population of normal controls, e.g., from a neonate or population of neonates of the same species subject to testing known to not be suffering from reversion to fetal consciousness, e.g., NMS. The threshold level can be determined from an individual or from a population of individuals. In the present diagnostic methods, levels of one or more compounds (e.g., neurosteroid, pregnane, androgen) above the threshold level is indicative and/or associated with reversion to fetal consciousness, e.g., NMS.

The terms "increased levels" or "elevated levels" are generally made with reference to a predetermined threshold level or a level of the one or more compounds (e.g., neurosteroid, pregnane, androgen, estrogen) in a biological sample of a neonate. An increased or elevated level is determined when the level of one or more compounds being measured in the test biological sample is at least about 10%, 25%, 50%, 75%, 100% (i.e., 1-fold), 2-fold, 3-fold, 4-fold or greater, in comparison to the predetermined threshold level of same one or more compounds (e.g., neurosteroid, pregnane, androgen, estrogen) in the same biological sample tissue type (e.g., blood or urine) obtained from the same species (e.g., an equine). In determining increased levels of one or more compounds from a biological sample, usually the same tissue types are compared.

The terms "subject," "individual," and "patient" interchangeably refer to any mammal, as described herein.

The term "biological sample" refers to a fluid sample from a neonate mammal, e.g., blood, serum, plasma, mucous, saliva, and/or urine.

As used herein, "administering" refers to local and systemic administration, e.g., including enteral, parenteral, pulmonary, and topical/transdermal administration. Routes of administration for compounds (e.g., one or more 5α reductase inhibitors) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intraarterial, transdermal and subcutaneous) administration.

The term "co-administering" or "concurrent administration", when used, for example with respect to the compounds (e.g., one or more 5α reductase inhibitor) and/or analogs thereof and another active agent, refers to administration of the compound and/or analogs and the active agent such that both are in the blood at the same time. Co-administration can be concurrent or sequential.

The term "effective amount" or "pharmaceutically effective amount" refer to the amount and/or dosage, and/or dosage regimen of one or more compounds necessary to bring about the desired result e.g., an amount sufficient to mitigating in a mammal one or more symptoms or behaviors associated with reversion to fetal consciousness, e.g., NMS, or an amount sufficient to lessen the severity of symptoms or behaviors associated with reversion to fetal consciousness, e.g., NMS, an amount sufficient to reduce the risk or prevent the occurrence of symptoms or behaviors associated with reversion to fetal consciousness, e.g., NMS in a mammal (e.g., prophylactically effective amounts).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies (e.g., reversion to fetal consciousness, e.g., NMS), or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease (e.g., reversion to fetal consciousness, e.g., NMS).

As used herein, the phrase "consisting essentially of" refers to the genera or species of active pharmaceutical agents recited in a method or composition, and further can include other agents that, on their own do not have substantial activity for the recited indication or purpose.

BRIEF DESCRIPTION OF THE DRAWINGS

FIGS. 2A-E illustrate median plasma steroid concentrations (ng/ml) of a) androstenedione, b) dehydroepiandrosterone (DHEA), c) epitestosterone, d) progesterone and e) pregnenolone for healthy, sick control and neonatal maladjustment syndrome (NMS) foals during the first 48 h of life.

DETAILED DESCRIPTION

1. Introduction

Figure 1:
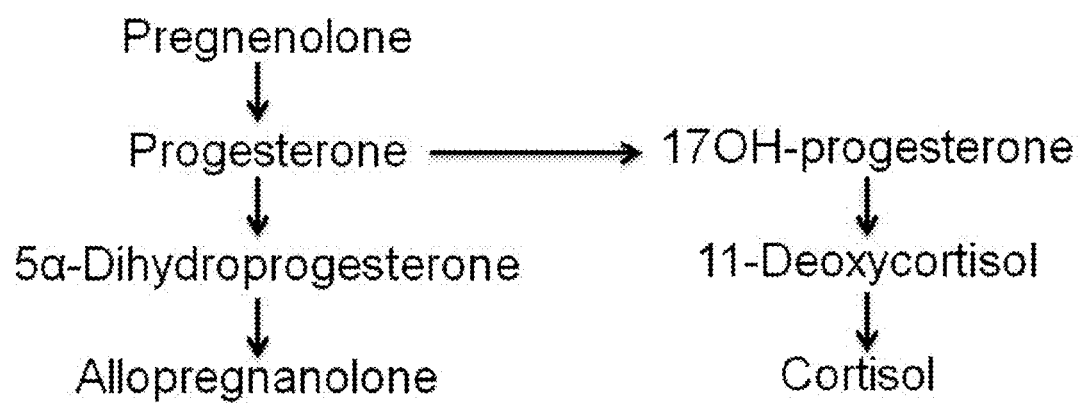
FIG. 1 illustrates a diagram of progestagens.

The present invention is base, in part, on the discovery that NMS is comprised of more than one phenotype; i) foals with hypoxia and ischemia and ii) foals with persistence of fetal hypothalamic pituitary adrenocortical (HPA) axis and elevated pregnane (e.g., pregnenolone, progesterone and metabolites) concentrations which can recover rapidly with no apparent residual neurological deficits. Studies presented herein determine the steroid profile of foals with NMS and compare it with that of foals with other neonatal diseases and healthy control foals.

The present invention is based, in part, on the discovery, that neurosteroid (e.g., pregnane) concentrations of ill, neonatal foals remain elevated following birth, reflective of a delayed, or interrupted, transition from intra- to extra-uterine life. Accordingly, one or more progesterone and pregnenolone measurements following birth is useful in aiding diagnosis of NMS.

2. Subjects Who May Benefit

The methods of diagnosis and treatment of a syndrome of reversion to fetal consciousness (e.g., equine neonatal maladjustment syndrome) find use to diagnose prevent, reduce, mitigate and/or treat reversion to fetal consciousness in any mammal, including humans and non-human mammals. Illustrative non-human mammals who can benefit from the present diagnostic and treatment methods include, e.g., Equidae (e.g., horse, ass, zebra), Bovidae (e.g., cattle, bison, sheep, goat, yak, impala, antelope, hartebeest, wildebeest, gnu, gazelle, water buffalo, duiker), Cervidae (e.g., deer, elk, moose, reindeer, pudu, bororo, brocket, guemal, muntjac), Suidae (e.g., pig, hog, boar), Canidae (domesticated dog, wolf, fox, coyote, jackel), Felidae (e.g., domesticated cat, cheetah, ocelot, lynx, bobcat, mountain lion, leopard, puma, lion, jaguar, tiger), Rodentia (e.g., mouse, rat, guinea pig, chinchilla, agouti, porcupine, beaver, gopher), Lagomorpha (e.g., rabbit, jackrabbit, hare, pika), Camelidae (e.g., camel, llama, alpaca, guanaco, vicugna), Ursidae (e.g., bear, panda), Procyonidae (e.g., raccoon, coati, olingo), Mustelidae (polecat, weasel, ferret, mink, fisher, badger, otter, wolverine, marten, sable, ermine), Elephantidae (e.g., elephant), rhinoceros, hippopotamus and non-human primates (e.g., chimpanzee, bonobo, macaque, ape).

The neonate may or may not be exhibiting symptoms of reversion to fetal consciousness or NMS (e.g., diminished mentation, inability and/or unwillingness to breathe properly using lungs, inability and/or unwillingness to nurse, poor affinity with dam, inability to stand and/or unstable gait). In varying embodiments, the neonate is less than 120 hours post birth, e.g., less than 96, 84, 72, 60, 48, 36, 24, 12, 9, 6, 3, 2, 1 hours post birth.

3. Methods of Diagnosis a. Measuring Levels of One or More Neurosteroids (e.g., Pregnanes) in a Biological Sample In varying embodiments of the diagnostic methods, the levels of one or more neurosteroids (e.g., pregnanes) in a biological sample from a neonate are measured.

In varying embodiments, the one or more neurosteroids measured or assayed comprise one or more pregnanes, one or more androgens and/or one or more estrogens. In varying embodiments, the panel of neurosteroids assayed or measured comprises one or more or all pregnanes selected from the group consisting of allopregnanolone (3α-hydroxy-5α-pregnan-20-one or 3α,5α-tetrahydroprogesterone; also abbreviated as THP or THPROG), allopregnanolone sulfate, 5α-dihydroprogesterone (DHP), 17-hydroxypregnenolone, 17-hydroxyprogesterone, pregnanediol, pregnenolone, pregnenolone sulfate and progesterone; one or more or all androgens/estrogens selected from the group consisting of androstenedione, 1,4-androstadiene-3, 17-1, boldenone, boldenone sulfate, dehydroepiandrosterone (DHEA), 5-α dihydroandrolone, 5-α dihydrotestosterone, 5-β dihydrotestosterone, epinandrolone, epistestosterone, 17-α estradiol, 17-β estradiol, 17-β estradiol sulfate, 5-α-estran-3-β-17 diol, estrone, estrone sulfate, 6-α-hydroxyandrostenedione, nandrolone, nandrolone glucuronide, nandrolone sulfate, 19-norandrostenedione, 19-nor-androsterone, 19-norepiandrosterone, testosterone, testosterone glucuronide and testosterone sulfate. Additionally, one or more or all compounds selected from the group consisting of adrenocorticotropic hormone (ACTH), adenosine, cortisol and oxytocin may be assayed or measured.

As discussed above, the one or more pregnanes measured generally have a 21-carbon nucleus and may have neurosteroidal activity. In varying embodiments, the pregnanes measured comprise adrenally-derived pregnanes. In some embodiments, one or more, e.g., one, two, three or four pregnanes selected from the group consisting of progesterone, pregnenolone, 17OH progesterone and pregnanediol are measured. In some embodiments, one or more pregnanes selected from the group consisting of progesterone and pregnenolone are measured. In varying embodiments, the levels of pregnenolone in the biological sample are measured. In varying embodiments, the level of one or more, e.g., 1, 2, 3, 4, 5, 6, 7, 8 or 9, pregnanes selected from the group consisting of allopregnanolone (3α-hydroxy-5α-pregnan-20-one or 3α,5α-tetrahydroprogesterone; also abbreviated as THP or THPROG), allopregnanolone sulfate, 5α-dihydroprogesterone (DHP), 17-hydroxypregnenolone, 17-hydroxyprogesterone, pregnanediol, pregnenolone, pregnenolone sulfate and progesterone is measured or assayed. In some embodiments, one or more, e.g., one, two, three or four pregnanes, selected from the group consisting of progesterone, pregnenolone, 17OH progesterone and pregnanediol are measured. In some embodiments, one or more pregnanes selected from the group consisting of progesterone and pregnenolone are measured. In varying embodiments, the levels of pregnenolone in the biological sample are measured. The levels of the one or more pregnanes in the biological sample can be compared with a predetermined threshold level.

In some embodiments, the level of one or more, e.g., 1, 2, 3, 4, 5, 6, 7, 8, 9, 10, 11, 12, 13, 14, 15, 16, 17, 18, 19, 20, 21, 22, 23, 24, 25, 26 or 27, androgens/estrogens selected from the group consisting of androstenedione, 1,4-androstadiene-3, 17-1, boldenone, boldenone sulfate, dehydroepiandrosterone (DHEA), 5-α dihydroandrolone, 5-α dihydrotestosterone, 5-β dihydrotestosterone, epinandrolone, epistestosterone, 17-α estradiol, 17-β estradiol, 17-β estradiol sulfate, 5-α-estran-3-β-17 diol, estrone, estrone sulfate, 6-α-hydroxyandrostenedione, nandrolone, nandrolone glucuronide, nandrolone sulfate, 19-norandrostenedione, 19-nor-androsterone, 19-norepiandrosterone, testosterone, testosterone glucuronide and testosterone sulfate is assayed or measured.

In varying embodiments, the level of one or more compounds selected from the group consisting of adrenocorticotropic hormone (ACTH), adenosine, cortisol and oxytocin is additionally assayed or measured.

In varying embodiments, the biological sample is a fluid sample, e.g., blood, serum, plasma, urine and/or saliva. In some embodiments, the fluid sample is blood. In some embodiments, the fluid sample is urine.

In varying embodiments, the neonate is less than 120 hours post birth, e.g., less than 96, 84, 72, 60, 48, 36, 24, 12, 9, 6, 3, 2, 1 or fewer hours post birth.

In varying embodiments, the neurosteroid (e.g., pregnane) levels are measured at two or more time points, e.g., two, three, four, five or more time points. For example, two or more measurements of neurosteroid (e.g., pregnane) levels may be performed, e.g., every 4, 6, 8, 10, 12, 14, 16, 18, 20, 24 or 48 hours, as appropriate.

The one or more neurosteroid (e.g., pregnane) compounds can be detected using any method known in the art. In varying embodiments, the one or more neurosteroid (e.g., pregnane) compounds are detected one or more known techniques, including, e.g., mass spectrometry (e.g., liquid chromatography mass spectrometry (LC-MS), gas chromatography mass spectrometry (GC-MS), tandem mass spectrometry (MS-MS), matrix-assisted laser desorption/ionization (MALDI), etc.), nuclear magnetic resonance (NMR), high performance liquid chromatography (HPLC), ultra-performance liquid chromatography (UPLC), atmospheric-pressure chemical ionization (APCI) or immunoassay (e.g., enzyme-linked immunoassay (ELISA), radioimmunoassay RIA), lateral flow immunoassay, etc.). See, e.g., Keski-Rahkonen, et al., *J Steroid Biochem Mol. Biol.* (2011) 127(3-5):396-404; Rauh, *J Steroid Biochem Mol. Biol.* (2010) 121(3-5):520-7; Kushnir, et al., *Clin Biochem.* (2011) 44(1):77-88; Kulle, et al., *J Endocrinol Invest.* (2011) 34(9):702-8; Tripathy, et al., *Clin Chim Acta.* (2012) 413(1-2):262-8; and Posthuma-Trumpie, et al., *Anal Bioanal Chem.* (2008) 392(6):1215-23.

b. Comparing the Measured Levels of Neurosteroids (e.g., Pregnanes) to a Threshold Level Levels of the one or more neurosteroids, e.g., the one or more pregnanes and/or the one or more androgens/estrogens above the predetermined threshold level indicate and/or are associated with a positive diagnosis of reversion to fetal consciousness. The increased or elevated levels of one or more measured neurosteroids is indicated by a detectable signal. In varying embodiments, the levels of the one or more measured neurosteroid (e.g., pregnane) compounds in a test sample can be compared to the levels of the one or more measured neurosteroid (e.g., pregnane) compounds from a negative or normal control sample or to a threshold value. In some embodiments, increased levels of one or more neurosteroids (e.g., pregnanes) are detected, and a diagnosis of reversion to fetal conscious, e.g., NMS, is indicated, e.g., when the neonate is exhibiting symptoms and/or the test sample has one or more neurosteroid (e.g., pregnane) compounds at levels elevated at least about 10%, 20%, 30%, 50%, 75% greater in comparison to the levels of the same neurosteroid (e.g., pregnane) compounds in the normal control sample or the predetermined threshold value. In some embodiments, increased levels of one or more neurosteroids (e.g., pregnanes) are detected, and a diagnosis of reversion to fetal conscious, e.g., NMS, is indicated, e.g., when the neonate is exhibiting symptoms and/or the test sample has one or more neurosteroid (e.g., pregnane) compounds at levels elevated at least about 1-fold, 2-fold, 3-fold, 4 fold or more, greater in comparison to the levels of the same neurosteroid (e.g., pregnane) compounds in the normal control sample or the predetermined threshold value. Usually, the sample and control or predetermined threshold levels are from the same tissue types.

In some embodiments, the levels of the one or more neurosteroid (e.g., pregnane) compounds in a test sample are compared with the levels of the one or more measured neurosteroid (e.g., pregnane) compounds from a positive control biological sample of a neonate known to suffer from reversion to fetal consciousness, e.g., NMS. In this case, levels of the one or more measured neurosteroid (e.g., pregnane) compounds in the test biological sample equivalent to or greater than the positive control sample, from a neonate known to suffer from reversion to fetal consciousness, e.g., NMS, are indicative of and/or associated with a positive diagnosis of reversion to fetal consciousness, e.g., NMS. Usually, the sample and control or predetermined threshold levels are from the same tissue types.

Alternatively, if the levels of the one or more measured neurosteroid (e.g., pregnane) compounds in the test biological sample are less than the levels of the one or more measured neurosteroid (e.g., pregnane) compounds in the positive control sample or the predetermined threshold level, then a diagnosis of reversion to fetal consciousness, e.g., NMS, is generally not indicated. Likewise, if the levels of the one or more measured neurosteroid (e.g., pregnane) compounds in the test biological sample are equivalent to or less than a negative or normal control sample or the predetermined threshold level, then a diagnosis of reversion to fetal consciousness, e.g., NMS, is not indicated.

In varying embodiments, the predetermined threshold level for the neurosteroids selected from allopregnanolone (3α-hydroxy-5α-pregnan-20-one or 3α,5α-tetrahydroprogesterone; also abbreviated as THP or THPROG), allopregnanolone sulfate, 5α-dihydroprogesterone (DHP), 17-hydroxypregnenolone, 17-hydroxyprogesterone, pregnanediol, pregnenolone sulfate, 1,4-androstadiene-3, 17-1, boldenone, boldenone sulfate, 5-α dihydroandrolone, 5-α dihydrotestosterone, 5-β dihydrotestosterone, epinandrolone, 17-α estradiol, 17-β estradiol, 17-β estradiol sulfate, 5-α-estran-3-β-17 diol, estrone, estrone sulfate, 6-α-hydroxyandrostenedione, nandrolone, nandrolone glucuronide, nandrolone sulfate, 19-norandrostenedione, 19-nor-androsterone, 19-norepiandrosterone, testosterone, testosterone glucuronide and testosterone sulfate, adrenocorticotropic hormone (ACTH), adenosine, cortisol and oxytocin is above 0.0001 ng/mL or any detectable level. In varying embodiments, the predetermined threshold level for androsterone, DHEA, epitestosterone, progesterone and pregnenolone at ages 0-few hours of age, 24 h, and 48 h old are as shown in Table 1. In varying embodiments, the threshold value for ACTH is 53 ng/mL), the threshold value for cortisol is 16 ng/mL, the threshold value for adenosine is 0.3 ng/mL), and the threshold value for oxytocin is 1.1 ng/mL.

TABLE 1

| Steroid (ng/mL) | 0 h | 24 h | 48 h |
|---|---|---|---|
| androstenedione | 0.6 | 0.3 | 0.0001 (any detectable level) |
| DHEA | 50 | 25 | 8 |
| epitestosterone | 0.2 | 0.05 | 0.004 |

TABLE 1-continued

| Steroid (ng/mL) | 0 h | 24 h | 48 h |
|---|---|---|---|
| progesterone | 4 | 0.0001 (any detectable level) | 0.0001 (any detectable level) |
| pregnenolone | 1200 | 193 | 104 |

Illustrative blood, serum or plasma threshold levels of pregnenolone in a neonate equine at 0h, 24 h and 48 h post birth are at least about 6000 ng/ml at 0-24 h post birth, at least about 550 ng/ml at 24-48 h post birth and at least about 315 ng/ml at about 48 h post birth and thereafter. In varying embodiments, the elevated pregnenolone levels are above about 12,900 ng/ml under 24 hours post birth, above about 3470 ng/ml at 24-28 hours post birth and/or above about 3420 ng/ml at or after 48 hours post birth. In varying embodiments, the elevated progesterone levels are above about 10.5 ng/ml under 24 hours post birth, above about 0.8 ng/ml at 24-28 hours post birth and/or above about 0.1 ng/ml at or after 48 hours post birth. In varying embodiments, the elevated progesterone levels are above about 9.7 ng/ml at 24-28 hours post birth and/or above about 14.3 ng/ml at or after 48 hours post birth.

c. Providing a Diagnosis

Upon a positive determination of elevated levels of one or more neurosteroids (e.g., pregnanes) in the biological sample of the subject, a positive diagnosis of reversion to fetal consciousness (e.g., NMS) may be provided. The subject may also be exhibiting one or more symptoms consistent with reversion to fetal consciousness (e.g., NMS). In varying embodiments, the diagnosis is provided to the parents of a human neonate or to the guardian/owner of a non-human neonate. In addition to providing a positive diagnosis, options for treatment may be provided, e.g., to prevent, reduce, inhibit, mitigate and/or reverse one or more symptoms associated with reversion to fetal consciousness (e.g., NMS).

4. Methods of Treatment

Upon a positive determination of elevated levels of one or more neurosteroids (e.g., pregnanes) and a diagnosis of reversion to fetal consciousness, the neonate can be treated by pharmacological (e.g., administration of an effective amount of a 5α reductase inhibitor) or physical (e.g., squeezing and/or hugging) means, or a combination of both pharmacological and physical methods.

a. Pharmacological Methods

In some embodiments, a neonate determined to be suffering from reversion to fetal consciousness, e.g., NMS, is administered an effective amount of a 5α reductase inhibitor. Illustrative 5α reductase inhibitors of use include, e.g., alfatradiol, dutasteride, finasteride, bexlosteride, episteride, izonsteride, lapisteride, turosteride, and analogs, salts and mixtures thereof.

i. Formulation

The one or more 5α reductase inhibitors, and salts and analogs thereof, can be administered orally, parenterally, (intravenously (IV), intramuscularly (IM), depo-IM, subcutaneously (SQ), and depo-SQ), sublingually, intranasally (inhalation), intrathecally, transdermally (e.g., via transdermal patch), topically, ionophoretically or rectally. In varying embodiments, the dosage form is selected to facilitate delivery to the brain (e.g., passage through the blood brain barrier). In this context it is noted that the one or more 5α reductase inhibitors described herein can be readily delivered to the brain. Dosage forms known to those of skill in the art are suitable for delivery of the one or more 5α reductase inhibitors.

Compositions are provided that contain therapeutically effective amounts of the compound. The one or more 5α reductase inhibitors are preferably formulated into suitable pharmaceutical preparations such as tablets, capsules, or elixirs for oral administration or in sterile solutions or suspensions for parenteral administration. Typically the one or more 5α reductase inhibitors described above are formulated into pharmaceutical compositions using techniques and procedures well known in the art.

The one or more 5α reductase inhibitors can be administered in the "native" form or, if desired, in the form of salts, esters, amides, prodrugs, derivatives, and the like, provided the salt, ester, amide, prodrug or derivative is suitable pharmacologically effective, e.g., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, orotic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

The one or more 5α reductase inhibitors or a physiologically acceptable salt or ester can be compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage to prevent, reduce and/or mitigate reversion to fetal consciousness, e.g., NMS, without inducing or eliciting adverse side effects in the neonate. In varying embodiments, the one or more 5α reductase inhibitors are administered at a dose that is in the range of about 10% to about 50% of a dose administered to an adult mammal of the same species, e.g., in the range of about 25 to about 30% of a dose that induces or elicits desired pharmacological effects in an adult mammal of the same species, e.g., about 10%, 15%, 20%, 25%, 30%, 35%, 40%, 45% or 50% of a dose administered to an adult mammal of the same species. The term "unit dosage from" refers to physically discrete units suitable as unitary dosages for mammals, each unit containing a predetermined quantity of active material calculated to produce the desired therapeutic effect, in association with a suitable pharmaceutical excipient.

Determination of an effective amount is well within the capability of those skilled in the art. Generally, an efficacious or effective amount of one or more 5α reductase inhibitors is determined by first administering a low dose or small amount of a 5α reductase inhibitor and then incrementally increasing the administered dose or dosages, until a desired effect is observed in the treated subject with minimal or no toxic side effects. Applicable methods for determining an appropriate dose and dosing schedule for administration of a combination of the present invention are described, for example, in Brunton, et al., *Goodman and Gilman's The Pharmacological Basis of Therapeutics,* 12th Edition, 2010, McGraw-Hill Professional; in a Physicians' Desk Reference (PDR), 66th Edition, 2012; in Loyd, et al., *Remington: The Science and Practice of Pharmacy,* 22nd Ed., 2012, Pharmaceutical Press; and in *Martindale: The Complete Drug Reference,* 37th Ed., Sweetman, 2011, Pharmaceutical Press., each of which are hereby incorporated herein by reference.

In varying embodiments, the dose of 5α reductase inhibitor administered to a neonate equine is about 1×, 2×, 5× or 10× the dose of 5α reductase inhibitor administered to an adult human. For example, in one embodiment, a dose of 0.1 mg/kg (5 mg total dose) dutasteride is administered to a neonate equine.

To prepare compositions, the one or more 5α reductase inhibitors are mixed with a suitable pharmaceutically acceptable carrier. Upon mixing or addition of the one or more 5α reductase inhibitors, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the one or more 5α reductase inhibitors in the selected carrier or vehicle. The effective concentration is sufficient for lessening or ameliorating at least one symptom of the disease, disorder, or condition treated and may be empirically determined.

Pharmaceutical carriers or vehicles suitable for administration of the one or more 5α reductase inhibitors provided herein include any such carriers known to those skilled in the art to be suitable for the particular mode of administration. In addition, the active materials can also be mixed with other active materials that do not impair the desired action, or with materials that supplement the desired action, or have another action. The one or more 5α reductase inhibitors may be formulated as the sole pharmaceutically active ingredient in the composition or may be combined with other active ingredients.

Where the one or more 5α reductase inhibitors exhibit insufficient solubility, methods for solubilizing may be used. Such methods are known and include, but are not limited to, using cosolvents such as dimethylsulfoxide (DMSO), using surfactants such as Tween™, and dissolution in aqueous sodium bicarbonate. Derivatives of the one or more 5α reductase inhibitors, such as salts or prodrugs may also be used in formulating effective pharmaceutical compositions.

The concentration of the one or more 5α reductase inhibitors is effective for delivery of an amount upon administration that lessens or ameliorates at least one symptom of the disorder for which the one or more 5α reductase inhibitors are administered and/or that is effective in a prophylactic context. Typically, the compositions are formulated for single dosage (e.g., daily) administration.

The one or more 5α reductase inhibitors may be prepared with carriers that protect them against rapid elimination from the body, such as time-release formulations or coatings. Such carriers include controlled release formulations, such as, but not limited to, microencapsulated delivery systems. The one or more 5α reductase inhibitors are included in the pharmaceutically acceptable carrier in an amount sufficient to exert a therapeutically useful effect in the absence of undesirable side effects on the patient treated. The therapeutically effective concentration may be determined empirically by testing the one or more 5α reductase inhibitors in known in vitro and in vivo model systems for the treated disorder (e.g., reversion to fetal consciousness, e.g., NMS). A therapeutically or prophylactically effective dose can be determined by first administering a low dose, and then incrementally increasing until a dose is reached that achieves the desired effect with minimal or no undesired side effects.

In various embodiments, the one or more 5α reductase inhibitors and/or analogs thereof can be enclosed in multiple or single dose containers. The one or more 5α reductase inhibitors and compositions can be provided in kits, for example, including component parts that can be assembled for use. For example, the one or more 5α reductase inhibitors can be provided in lyophilized form and a suitable diluent may be provided as separated components for combination prior to use. A kit may include one or more 5α reductase inhibitors and a second therapeutic agent for co-administration. The one or more 5α reductase inhibitors and second therapeutic agent may be provided as separate component parts. A kit may include a plurality of containers, each container holding one or more unit dose of the compounds. The containers are preferably adapted for the desired mode of administration, including, but not limited to food compositions (e.g., kibble, pellets, cookies), tablets, gel capsules, sustained-release capsules, and the like for oral administration; depot products, pre-filled syringes, ampules, vials, and the like for parenteral administration; and patches, medipads, creams, and the like for topical administration.

The concentration and/or amount of the one or more 5α reductase inhibitors in the drug composition will depend on absorption, inactivation, and excretion rates of the active compound, the dosage schedule, and amount administered as well as other factors known to those of skill in the art.

The one or more 5α reductase inhibitors may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the one or more 5α reductase inhibitors can be provided in a formulation that protects it from the acidic environment of the stomach. For example, the composition can be formulated in an enteric coating that maintains its integrity in the stomach and releases the one or more 5α reductase inhibitors in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the one or more 5α reductase inhibitors can be incorporated with excipients and used in the form of food compositions (e.g., kibble, pellets, cookies), tablets, capsules, or troches. Pharmaceutically compatible binding agents and adjuvant materials can be included as part of the composition.

In various embodiments, the food compositions (e.g., kibble, pellets, cookies), tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The one or more 5α reductase inhibitors can also be administered as a component of an elixir, suspension, syrup, wafer, chewing gum or the like. A syrup may contain, in addition to the one or more 5α reductase inhibitors, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropylene glycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The one or more 5α reductase inhibitors may be prepared with carriers that protect the one or more 5α reductase inhibitors against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

ii. Routes of Administration and Dosing

In various embodiments, the one or more 5α reductase inhibitors and/or analogs thereof can be administered orally, parenterally (IV, IM, depo-IM, SQ, and depo-SQ), sublingually, intranasally (inhalation), intrathecally, transdermally (e.g., via transdermal patch), topically, or rectally. Dosage forms known to those skilled in the art are suitable for delivery of the one or more 5α reductase inhibitors and/or analogs thereof.

In various embodiments, the one or more 5α reductase inhibitors and/or analogs thereof may be administered enterally or parenterally. When administered orally, the compounds can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compound needs to be administered only once or twice daily.

The oral dosage forms can be administered to the patient 1, 2, 3, or 4 times daily. It is preferred that the compound be administered either three or fewer times, more preferably once or twice daily. Hence, it is preferred that the compound be administered in oral dosage form. It is preferred that whatever oral dosage form is used, that it be designed so as to protect the compound from the acidic environment of the stomach. Enteric coated tablets are well known to those skilled in the art. In addition, capsules filled with small spheres each coated to protect from the acidic stomach, are also well known to those skilled in the art.

The one or more 5α reductase inhibitors and/or analogs thereof may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

In various embodiments, the one or more 5α reductase inhibitors and/or analogs thereof can be administered parenterally, for example, by IV, IM, depo-IM, SC, or depo-SC.

In various embodiments, the compounds and/or analogs thereof can be administered sublingually. When given sublingually, the compounds and/or analogs thereof can be given one to four times daily in the amounts described above for IM administration.

In various embodiments, the compounds and/or analogs thereof can be administered intranasally. When given by this route, the appropriate dosage forms are a nasal spray or dry powder, as is known to those skilled in the art. The dosage of compound and/or analog thereof for intranasal administration is the amount described above for IM administration.

In various embodiments, compound and/or analogs thereof can be administered intrathecally. When given by this route the appropriate dosage form can be a parenteral dosage form as is known to those skilled in the art. The dosage of compound and/or analog thereof for intrathecal administration is the amount described above for IM administration.

In certain embodiments, the compound and/or analog thereof can be administered topically. When given by this route, the appropriate dosage form is a cream, ointment, or patch. Because the amount that can be delivered by a patch is limited, two or more patches may be used. The number and size of the patch is not important, what is important is that a therapeutically effective amount of compound be delivered as is known to those skilled in the art. The compound can be administered rectally by suppository as is known to those skilled in the art.

It should be apparent to one skilled in the art that the exact dosage and frequency of administration will depend on the particular condition being treated, the severity of the condition being treated, the age, weight, general physical condition of the particular patient, and other medication the individual may be taking as is well known to administering physicians who are skilled in this art.

b. Physical Methods

In some embodiments, a neonate determined to be suffering from reversion to fetal consciousness, e.g., NMS, is subject to squeezing or hugging of the mid-thorax region. In varying embodiments, the squeezing and/or hugging applies uniform pressure along the mid-thorax region with a pressure and for a time period sufficient to mimic passage through the birth canal appropriate to the species of the subject. For example, in some embodiments, the applied pressure of the squeezing is maintained for at least 10 minutes, e.g., at least 15, 20, 25, 30, 35, 40, 45, 50, 55 or 60 minutes, as appropriate or necessary. The pressure may be applied one or more intervals, e.g., 1, 2, 3, 4, 5, or more intervals, as appropriate or necessary.

When the subject is a human, skin-on-skin contact is preferred, with the neonate's head placed near the heart of the person applying squeezing or hugging pressure (e.g., the mother). So-called Kangaroo Mother Care is known in the art and reviewed, e.g., in Moore, et al., *Cochrane Database Syst Rev.* (2012) May 16; (5):CD003519; Bailey, *Br J Hosp Med* (Loud). (2012) 73(5):278-81; Bulfone, et al., *Prof Inferm.* (2011) 64(2):75-82; Conde-Agudelo, et al., *Cochrane Database Syst Rev.* (2011) March 16; (3):CD002771; and Lawn, et al., *Int J Epidemiol.* (2010) 39 Suppl 1:1144-54.

In varying embodiments, pressure is applied by a rope or a cuff or a sleeve. For example, substantially uniform pressure can be applied by encircling the mid-thorax region of the neonate in an inflatable cuff or sleeve. In varying embodiments, the mid thorax region of the neonate is encircled and subject to pressure with an inflatable cuff or sleeve system. The inflatable cuff or sleeve can comprise a pneumatic inflating sleeve, e.g., similar to a blood pressure cuff. The cuff or sleeve can be constructed of a material or coated with a material that does not abrade or injure the neonate upon contact. The cuff or sleeve can be inflated to a predetermined pressure (e.g., to about 10 psi or less) over the proximal and mid thorax of the neonate (e.g., foal) and maintained at a pressure and for time period sufficient to mimic the birth canal, e.g., sufficient to provide deep touch pressure. In varying embodiments, the inflated cuff or sleeve provides substantially uniform pressure to the mid-thorax of the neonate. As appropriate, the inflatable cuff or sleeve can be inflated using a foot pump or an automated pump motor. The inflatable cuff or sleeve can be kept in place by use of straps. In varying embodiments, for inflatable cuffs or sleeves designed for use on quadruped mammals (e.g., equine neonates), the device can have straps designed to around the neonate's neck and between the front legs. The inflatable cuff or sleeve is provided in a size appropriate to the size of the species being treated, such that when inflated, the cuff or sleeve provides substantially uniform pressure to the mid-thorax region of the neonate. The inflatable cuff or sleeve can be designed to be a reusable device.

Figure 3:
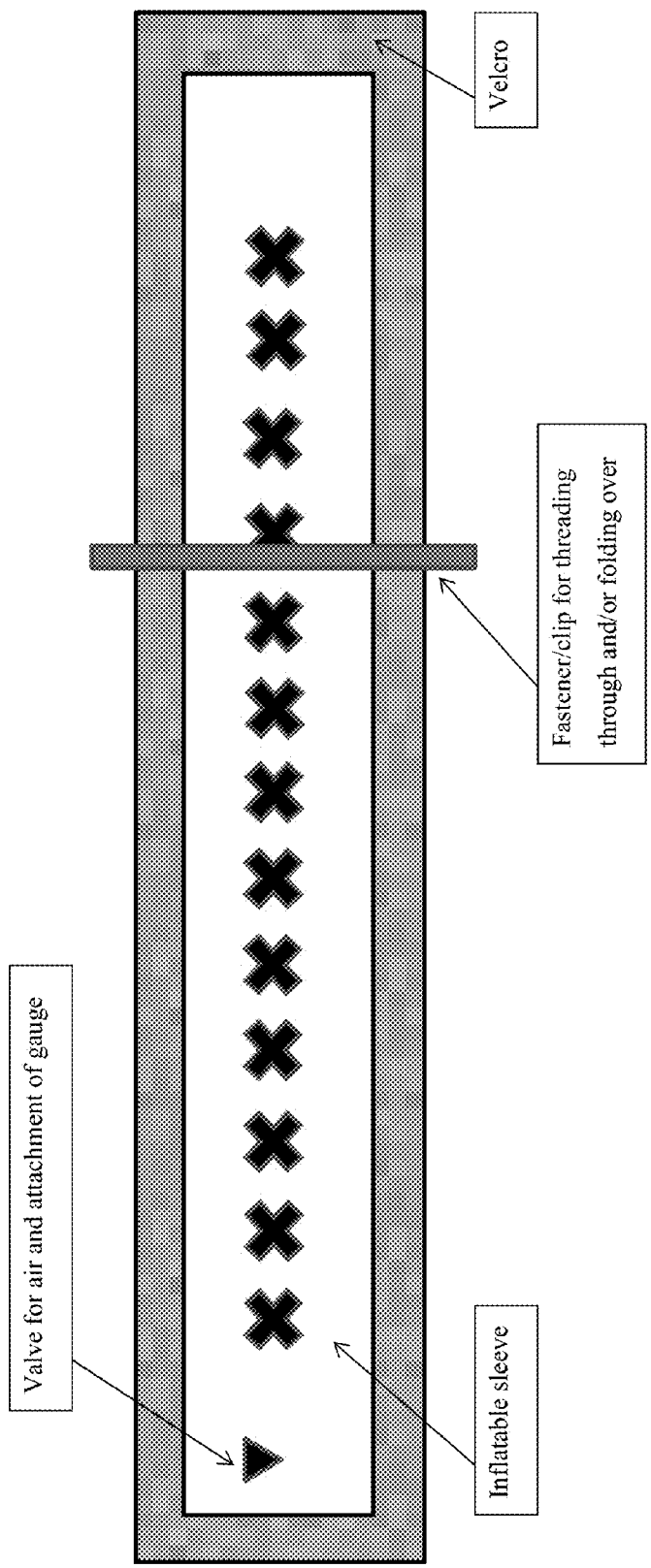
FIG. 3 illustrates features of an embodiment of an inflatable cuff useful for squeezing and imparting deep touch pressure to a neonate.
Figure 4:
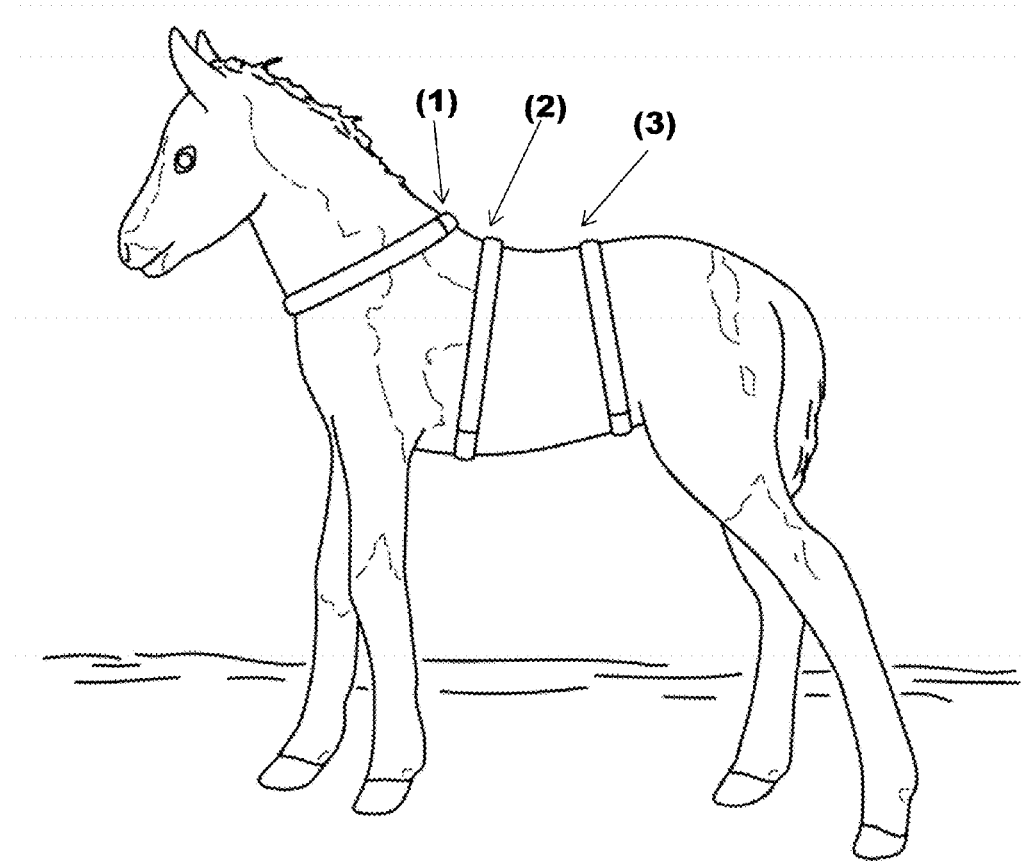
FIG. 4 illustrates an embodiment of tandem inflatable cuffs on a neonate equine. The cuffs are held in place with a strap (1) around the neonate's neck. An inflatable heart-girth cuff (2) and an inflatable caudal cuff (3) are depicted.
Figure 5:
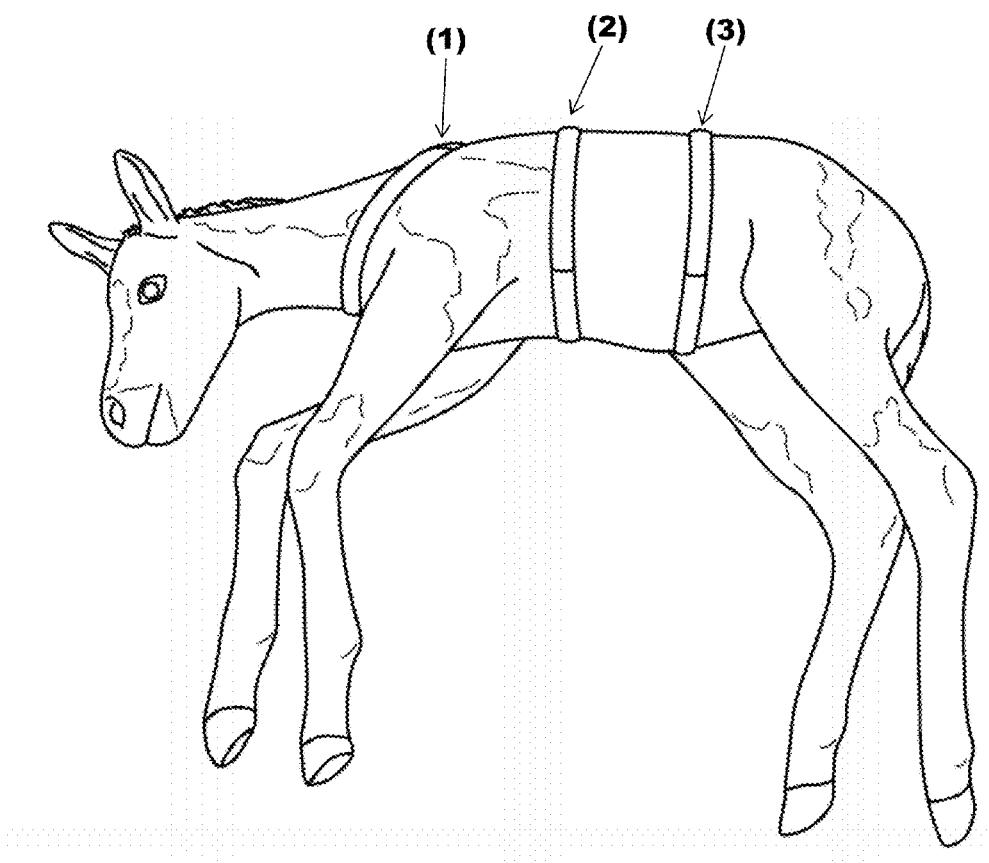
FIG. 5 illustrates an embodiment of tandem inflatable cuffs on a neonate equine. The cuffs are held in place with a strap (1) around the neonate's neck. An inflatable heart-girth cuff (2) and an inflatable caudal cuff (3) are depicted. The deep touch pressure of the inflated cuffs induces somnolence in the neonate.

In varying embodiments, multiple cuff or sleeve devices are used in tandem. For example, two pneumatic sleeves can be placed over the mid body, a first over the heart-girth area and a second over the caudal area—anywhere from ribs to abdomen. Each sleeve has a pneumatic inflation device to ensure constant pressure that does induce somnolence but does not impair ventilation (e.g., to about 10 psi or less). For use on equines and other quadrupeds, the sleeve can be placed on the neonate (e.g., the foal) when standing (FIG. 3). For applying the first device, a strap (e.g., canvas, leather or any appropriate material) can be placed around the neonate's neck to prevent the device from sliding caudally. In varying embodiments, the device can be secured around the thoracic circumference of the neonate through any appropriate means (e.g., by looping a strap, a metal hinge, a hook, a clasp, a belt). In one embodiment, the strap is folded back upon itself and can be pulled snugly or tightly and attached to Velcro. A hand or foot operated or automated airpump can be used to inflate the pneumatic sleeve, (inflatable sleeve in FIG. 4). The sleeve can be inflated to an internal pressure sufficient to exert a substantial squeezing pressure on the neonate. In varying embodiments, the cuffs or sleeves are inflated to about 10 psi. The pressure can be checked with an air gauge. The second device can be similarly applied, as illustrated in FIG. 3. The neonate then becomes laterally recumbent and stays that way for an appropriate period of time (e.g., 20-30 minutes). FIG. 5 shows the device attached on an equine foal with the strap around the neck to hold it in place. Upon completion of the squeezing procedure, the air is released from the sleeve and the sleeve is detached and the foal is allowed to wake up. Heart-girth measurements vary depending on species and breed but the device can be readily designed to fit any neonate, e.g., any equine foal of varying breeds less than 1 week of age. Typically, the cuffs or sleeves range from about 26 to about 48 inches in length, e.g., sufficient to encircle the circumference of a neonatal equine over the heart-girth area.

5. Methods of Monitoring

The elevated levels of one or more neurosteroids (e.g., pregnanes, e.g., pregnenolone) correlated with a syndrome of reversion to fetal consciousness (e.g., NMS) allows for the course of treatment for mitigating and/or reversing reversion to fetal consciousness (e.g., NMS) to be monitored. For methods of monitoring, one or more test biological samples are obtained from a subject undergoing treatment for mitigating and/or reversing reversion to fetal consciousness (e.g., NMS). As appropriate, biological samples are obtained from the subject at various time points, e.g., before, during, and/or after a course of treatment (e.g., physical and/or pharmacological). Levels of one or more neurosteroid (e.g., pregnane) compounds in the biological sample (e.g., pregnenolone) are then determined and compared to a reference biological sample which includes known levels of the one or more neurosteroids (e.g., pregnanes). In varying embodiments, the reference biological sample is from an untreated subject either known to suffer from reversion to fetal consciousness (e.g., NMS) or known to be normal. Generally, test and control biological samples are the same (e.g., blood, serum, plasma, urine).

In embodiments where the reference biological sample is from a normal control subject, a similarity in the levels of the one or more measured neurosteroids (e.g., pregnanes) in the test biological sample and the reference biological sample indicates that the treatment is efficacious. However, increased or elevated levels of one or more neurosteroids (e.g., pregnanes) in the test biological sample taken at one or more time points in comparison to levels of the same one or more neurosteroids (e.g., pregnanes) in a normal control reference biological sample indicates a less favorable clinical outcome or prognosis. Similarly, if the reference biological sample is from a control subject known to suffer from reversion to fetal consciousness (e.g., NMS), a decrease or reduction in levels of one or more of the measured neurosteroids (e.g., pregnanes, e.g., pregnenolone) in the test biological sample in comparison to levels of the same one or more pregnanes in the positive control reference biological sample indicates that the treatment is efficacious, while similar or elevated levels of the one or more neurosteroids (e.g., pregnanes) in the test population and the positive control reference biological sample indicates a less favorable clinical outcome or prognosis.

Additionally, the levels of the one or more neurosteroids (e.g., pregnanes) determined in a biological sample from a subject obtained after treatment (i.e., post-treatment levels) can be compared to the levels of the one or more neurosteroids (e.g., pregnanes) determined in a biological sample from the same subject obtained prior to treatment onset (i.e., pre-treatment levels). A decrease in the levels of the one or more neurosteroids (e.g., pregnanes) in a post-treatment sample indicates that the treatment is efficacious while an increase or maintenance in the levels of the one or more neurosteroids (e.g., pregnanes) in the post-treatment sample indicates a less favorable clinical outcome or prognosis.

As used herein, the term "efficacious" indicates that the treatment leads to a reduction in the levels of the one or more measured neurosteroids (e.g., pregnanes) in a subject that are associated with, correlative and/or indicative of reversion to fetal consciousness (e.g., NMS). When a treatment of interest is applied prophylactically, the term "efficacious" means that the treatment retards or prevents symptoms of reversion to fetal consciousness (e.g., NMS) from forming or retards, prevents, or alleviates one or more symptoms of reversion to fetal consciousness.

EXAMPLES

The following examples are offered to illustrate, but not to limit the claimed invention.

Example 1

Allopregnanolone Infusion Induced Neurobehavioural Alterations in a Neonatal Foal Materials and Methods A healthy neonatal 50 kg Quarter Horse colt from the research herd at the School of Veterinary Medicine, University of California, Davis was selected for the infusion. The foal was born from a healthy Quarter Horse mare with a normal gestational length without complications, and normal observed parturition except that the placental passage was prolonged. Although retention of the placenta for 7 h post birth is not considered normal by most standards, the placenta was evaluated and determined to be complete and normal. Further, the mare did not display any signs or complications associated with placental retention. The foal was deemed healthy based upon complete physical and neurological examinations immediately post birth. The foal exhibited normal adaptive behaviour with righting reflex, and time to stand and suckle within normal limits. Repeat physical and neurological examinations at age 6 h, immediately prior to infusion, were also normal.

Intravenous catheters were placed aseptically in the right jugular vein for sample collection and in the left jugular vein for infusion of allopregnanolone. Allopregnanolone (5 alpha-pregnan-3 alpha-ol-20-one; Steraloids Inc., Newport, R.I., USA) was dissolved in an ethanol-based solution to a total concentration of 9 mg/ml. Infused dose and concentration of allopregnanolone in this foal were determined based on concentrations reported in in vivo studies in the modulation of the HPA axis in male rats (Naert, et al., (2007) *Psychoneuroendocrinology* 32, 1062-1078). An initial bolus of 0.05 mg/kg bwt i.v. of allopregnanolone was given followed by a constant rate infusion (CRI) of 0.02 mg/kg bwt/min using an infusion pump. Based on clinical effects of the initial dosage, a second bolus of 0.1 mg/kg bwt i.v. was given after 5 min and followed by a CRI of 0.04 mg/kg bwt/min for 5 min. The infusion was discontinued for 30 min to allow observation of any neurobehavioural (NB) alterations, and then a final bolus of 0.2 mg/kg bwt i.v. was given.

Neurobehavioural alterations were recorded and graded through a NB scoring system developed by the authors for the assessment of foals with NMS (Table 2). From preliminary work, foals with NMS had scores >8 from a range of 0 (normal foal) to 20 (comatose with paroxysmal activity). Mentation was defined as: normal if the foal was alert and responsive; quiet to obtunded if the foal was apparently lethargic but responsive to external stimuli (e.g., touch, sound); stuporous if level of consciousness was decreased but responsive to painful stimuli (e.g. pinching skin with haemostats); and comatose if the foal lost consciousness and was unresponsive to any stimuli. Paroxysmal activity was defined as abnormal events such as seizures or seizure-like activity, rhythmic limb movements, tremors or paddling. The NB scores were calculated at 5 min intervals throughout the infusion period. Following the infusion, the foal was observed hourly for the first 6 h and then at 12 h intervals for 2 days.

TABLE 2

Neurobehavioral scoring system.

| Parameter | 0 | 1 | 2 | 3 |
|---|---|---|---|---|
| Mentation and reaction to stimuli | Normal, bright, alert responsive | Mildly obtunded, slightly decreased or increased reactivity to stimuli | Moderately obtunded, moderately decreased or increased reactivity to stimuli | Severely obtunded with hyper-reactivity to stimuli, to comatose |
| Ability to stand | Stands unassisted | Stands with minimal assistance | Stands with marked support | Unable to stand |
| Bonding to mare | Actively bonds with and follows mare | Slightly reduced interaction with mare | Aimless wandering or periods of reduced responsiveness to | Unaware of mare |
| Ability to nurse | Latches on and nurses effectively | Searches out teat but does not nurse vigorously | Weak, ineffective suckling | No suckling |
| Paroxysms | None | 0 | None, limb stretching, paddling | Seizures or seizure-like activity |
| Ear position | Erect | 0 | Ears partially erect | Floppy, no tone |

Paroxysms is defined as episodes of abnormal activity.

Heparinised blood samples were collected at birth, age 6 h and at 15 min intervals during the infusion. Blood was immediately centrifuged following collection and plasma stored at −80° C. until analysed by liquid chromatography mass spectrometry (LC-MS) utilising on-line sample extraction by turbulent flow chromatography (TFC) and detection by select reaction monitoring (SRM) on a triple quadrupole mass spectrometer. Samples were diluted 2:1 with water fortified with 4 internal standards: D3-testosterone, D3-boldenone, D7-androstenedione and D3-testosterone sulphate. Analytes were separated by liquid chromatography using a Thermo TLX-2

TFC system with a Thermo Cyclone P extraction column and an ACE C18 analytical column. Analytes were introduced by electrospray ionisation to a Thermo TSQ Vantage triple-quadrupole mass spectrometer operating in both negative and positive modes. Free concentrations of 34 steroids were monitored in one analytical method over a 24-min run time. Detection and quantitation was accomplished using 3 or more SRM transitions per compound for all compounds other than 17-hydroxy pregnenolone where single ion monitoring (SIM) was utilised. This method was validated and the following assessed for each analyte: linearity, limit of detection, limit of quantitation, accuracy, precision, matrix effects, extraction recovery and potential endogenous interferences. The following steroids were analysed: allopregnanolone, dehydroepiandrosterone (DHEA), 5-alpha dihydroprogesterone, 17-hydroxy pregnenolone, pregnenolone, pregnanediol and progesterone. A diagram of the relation of these neurosteroids is shown in FIG. 1.

For NB comparison, a second age-matched clinically healthy neonatal Quarter Horse colt was infused with 99.9% ethanol diluted with 0.9% saline to a final concentration of 5% ethanol without allopregnanolone. Infusion of this solution followed the same protocol (dosage [based on 5% ethanol] and rate) of administration as for the first foal. The study was approved by an Animal Care and Use protocol from University of California, Davis.

onlinelibrary.wiley.com/doi/10.1111/j .2042-3306.2011.00504.x/full)). Clinical signs persisted during the constant rate infusion. Within 8 min of cessation of the infusion the foal began to show signs of increased responsiveness. By 15 min after cessation of the infusion or the final bolus the foal was standing but continued to show clinical signs of mild obtundation, reduced coordination and poor udder seeking ability (NB score of 9; File S5 (published on online with Madigan, et al., Equine Veterinary Journal 44, Suppl. 41 (2012) 109-112; accessible on the internet at onlinelibrary.wiley.com/doi/10.1111/j .2042-3306.2011.00504.x/full)). The foal appeared normal by 30 min after infusion of the neurosteroid (NB score of 0; File S6 (published on online with Madigan, et al., Equine Veterinary Journal 44, Suppl. 41 (2012) 109-112; accessible on the internet at onlinelibrary.wiley.com/doi/10.1111/j.2042-3306.2011.00504.x/full)).

No long-term NB effects were observed following the infusion. The control foal's NB scores were unchanged throughout the infusion. Steroid concentrations from Foal 1 are detailed in Table 3; these were not measured in the control foal due to lack of NB alterations, cost and probability of undetectable concentrations of neurosteroids. Due to an increase in dehydroepiandrosterone (DHEA) concentrations between birth and age 6 h, luteinising hormone (LH) concentrations at various time points were measured to investigate if this rise was due to production by the testis. However, there was no change in LH concentration.

TABLE 3

Steroid concentrations and NB score (0-20) in a healthy foal infused with allopregnanolone

| Age (hours) | Time point | Neurobehavior score | ACTH (pmol/L) | Cortisol (nmol/L) | DHEA | 17-OH pregnenolone |
|---|---|---|---|---|---|---|
| 0 | 10 minutes post-birth | 0 | NP | NP | 37,940 | 1,295,070 |
| 6 | Pre-infusion | 0 | 3.4 | 64 | 86,593 | 91,877 |
| 6¼ | Bolus 0.05 mg/kg IV, CRI 0.02 mg/kg/min | 14 | 2.1 | 58 | 74,475 | 73,982 |
| 6½ | 15 minutes post initial infusion | 8 | 2.6 | 55 | 1,232,216 | 95,275 |
| 6¾ | Bolus 0.2 mg/kg IV | 15 | 4.7 | 40 | 56,910 | 57,581 |

| Age (hours) | Progesterone | Pregnenolone | 5-α Dihydroprogesterone | Allopregnanolone | Pregnanediol |
|---|---|---|---|---|---|
| 0 | 3,126 | 3,074,455 | ND | ND | 110,674 |
| 6 | 880 | 1,279,409 | ND | ND | 67,134 |
| 6¼ | 776 | 1,252,565 | 18,065 | 478,909 | 63,241 |
| 6½ | 1,189 | 1,206,684 | 18,842 | 126,566 | 73,497 |
| 6¾ | 646 | 1,144,544 | 28,406 | 466,208 | 79,574 |

All concentrations are in pg/mL unless stated, neurobehavioral score (0-18),
DHEA = dehydroepiandrosterone,
NP = not performed,
ND = not detected.

Results

Prior to the allopregnanolone infusion, the colt was bright, alert and responsive (NB score of 0; File S1 (published on online with Madigan, et al., Equine Veterinary Journal 44, Suppl. 41 (2012) 109-112; accessible on the internet at onlinelibrary.wiley.com/doi/10.1111/j.2042-3306.2011.00504.x/full). Infusion of 0.05 mg/kg bwt allopregnanolone followed by a CRI at 0.02 mg/kg bwt/min resulted in signs of sedation and decreased responsiveness to the environment (NB score of 14). Infusion of higher concentrations of allopregnanolone (0.1 and 0.2 mg/kg bwt) resulted in dramatic NB effects with the foal becoming recumbent, stuporous, unresponsive to the mare, environment, sound and tactile stimulation (NB score of 16; File S2S4 (published on online with Madigan, et al., Equine Veterinary Journal 44, Suppl. 41 (2012) 109-112; accessible on the internet at Discussion Infusion of allopregnanolone to a healthy foal in this study produced marked NB effects. This is consistent with the clinical use of certain steroidal drugs, such as alphaxalone, as anaesthetic agents in male rats (Naert, et al., (2007) Psychoneuroendocrinology 32:1062-1078). Allopregnanolone in other species has been shown to cross the blood-brain barrier and is thought to mediate its effects in the central nervous system (CNS) via the GABAA receptor (Zhu, et al., (2001) Br J Anaesth 86:403-412). Infusion of allopregnanolone in this healthy foal provided evidence that 5-alpha reduced pregnanes can cross the blood-brain barrier and have effects in the CNS. Allopregnanolone concentrations peaked in conjunction with maximum NB effects following infusion. The rapid recovery from NB alterations with no apparent residual deficits once the infusion was discontinued, suggested that allopregnanolone was quickly metabolised in this healthy foal. Similar rapid dampening effects in the CNS and recovery were observed with the use of the neurosteroid anaesthetic alphaxalone in ponies undergoing castration (Leece, et al., (2009) *Vet Anaesth Analg* 36, 480-484). As allopregnanolone is apparently metabolised rapidly, the clinical signs associated with NMS in foals would be expected to dissipate rapidly. However, clinical manifestations of NMS can last several days, suggesting ongoing persistent production and release of allopregnanolone or other neurosteroids responsible for such observations. It is also unclear what triggers and stops these events in affected foals. Progestagen levels in this healthy foal decreased with age and are in agreement with the results of previous work (Holtan, et al., (1991) *J Reprod Fert Suppl* 44:517-528). The rise in DHEA between birth and age 6 h in this foal appeared to be neither testicular nor adrenal in origin as determined by constant levels of luteinising hormone and pregnanes, respectively, and was therefore deemed unlikely to be of biological relevance.

Recently, higher plasma concentrations of progesterone, epitestosterone and androstenedione were found in NMS foals compared with foals with other disorders. Findings from that work (Aleman, et al. (2013) *Equine Vet J* 45:661-665), along with the NB alterations induced by the infusion of allopregnanolone are consistent with the conclusion that NMS is in part a manifestation of persistent fetal HPA status mediated and sustained by elevated concentrations of progestagens as occurs naturally in the fetus (Warnes, et al., (2004) *Biol Reprod* 71:620-628). The fetus must rapidly change from the quiet suppressed state in utero to one of arousal, and attempts to rise shortly after birth. A failure of the transition from the fetal HPA status to immediately post birth signals to engage the newborn into normal post foaling neurobehaviour may be the cause or involved in part in the pathogenesis of NMS. Further, the measured neurosteroids and altered neurological status in this study suggest that neurosteroids readily cross the blood-brain barrier and exert altering CNS effects compatible with NMS in affected foals. Certainly some foals suffer severe birth hypoxia and recover, and have been included in the broad description of NMS. However, the recovery from severe birth hypoxia would be expected to be slow and likely to have residual neurological deficits as documented in all other mammalian species suffering severe birth hypoxia (McAuliffe, et al., *Brain Res* (2006) 1118:208-221). Ongoing production of pregnanes by the foal's brain and adrenal glands causes the clinical signs observed in foals with NMS and rapid recovery of signs with no apparent residual deficits is compatible with the decline of pregnane-mediated sedative type effects (Zhu, et al., (2001) *Br J Anaesth* 86:403-412).

It is unclear how foals that are normal at birth develop NMS within the first 48 h of life. However, a similar mechanism reported in neonatal sheep may occur whereby neonatal stress can increase allopregnanolone production by the brain and release of deoxycorticosterone from the adrenal glands, which the brain metabolises into 5α-tetrahydrodeoxycorticosterone (TH-DOC), another CNS depressant (Hirst, et al., (2008) *Neurochem Int* 52, 602-610). Obtundation, seizures and hyperaesthesia are common signs of NMS. Whilst the infused neuroactive steroid allopregnanolone has a dampening effect in the CNS, others within the large spectrum of neurosteroids, including metabolites of allopregnanolone, have excitatory effects that may be associated with seizures and hyperaesthesia (Rogawski and Reddy, (2004) Neurosteroids: Endogenous modulators of seizure susceptibility. In: Epilepsy: Scientific Foundations of Clinical Practice, Eds: Rho, et al., Marcel Dekker, New York. pp 319-355). Neurosteroid concentrations in clinical NMS are likely to be a far more complex condition than that represented by infusion of one compound.

Example 2

Abnormal Plasma Neurosteroid Concentrations in Ill, Neonatal Foals Presented to the Neonatal Intensive Care Unit Materials and Methods Foals.

The NMS foal group (n=32; 15 colts and 17 fillies) and the other neonatal disease foal group (n=12; 4 colts and 8 fillies) were comprised of foals admitted to the University of California, Davis Veterinary Medical Teaching Hospital in 2008 and Rossdale and Partners, Newmarket, UK in 2010 and 2011 (Aleman, et al. (2013) *Equine Vet J* 45:661-665). To be included as a foal with NMS, other disorders with a similar clinical presentation, such as prematurity and sepsis, were ruled out based on a minimum data base (published sepsis score, complete blood count, chemistry panel, blood gases, indirect blood pressure, central venous pressure, blood culture, urinalysis, abdominal ultrasound, and carpi, tarsi, thoracic and abdominal radiography) (Brewer and Koterba (1988) *Equine Vet J* 20, 18-22). Foals with a sepsis score of 11 or greater were additionally classed as septic (Brewer and Koterba (1988), supra). Historical knowledge of pre-, intra- or post-natal hypoxia was recorded. Clinical signs of NMS included altered mentation (obtunded, stuporous, comatose), decreased bonding to the mare, vocalization, aimless wandering, hyper- or lack of reactivity to stimuli, seizures, and abnormal ear position. Foals were subjectively scored by the attending clinician as mild-moderate if able to nurse and ambulate with help, or severe if recumbent and unable to nurse, even with help. Case details of NMS foals are given in Table 4. Foals in the other neonatal disease group (sick, non-NMS controls) were randomly selected based on client consent and availability of the authors for sample collection. These foals had a variety of clinical diagnoses (Table 5).

TABLE 4

Case histories of neonatal maladjustment syndrome (NMS) foal group (n = 32).

| Case | Gender | Age (h) | Outcome | Clinical history of hypoxia | Other diagnosis | Sepsis score | Severity | Creatinine (umol/L) | PMN (×10⁹/l) |
|---|---|---|---|---|---|---|---|---|---|
| 1 | M | 0 | S | No | No | 10 | Sev | 1800 | 10.25 |
| 2 | M | 24 | S | No | No | 6 | M-M | 1030 | 5.44 |
| 3 | M | 24 | S | No | No | 6 | M-M | 110 | 7.68 |
| 4 | M | 0 | S | Caesarean | Sepsis | 12 | Sev | 247 | 2.15 |
| 5 | F | 0 | S | Caesarean | No | 8 | M-M | 330 | 6.25 |
| 6 | F | 0 | S | Dystocia | No | 6 | M-M | 242 | 10.57 |

TABLE 4-continued

Case histories of neonatal maladjustment syndrome (NMS) foal group (n = 32).

| Case | Gender | Age (h) | Outcome | Clinical history of hypoxia | Other diagnosis | Sepsis score | Severity | Creatinine (umol/L) | PMN ($\times 10^9$/l) |
|---|---|---|---|---|---|---|---|---|---|
| 7 | F | 0 | S | No | No | 2 | M-M | 107 | 12.26 |
| 8 | F | 0 | S | Dystocia | Carpal contracture | 7 | M-M | 237 | 7.55 |
| 9 | F | 0 | S | No | Sepsis, meconium aspiration, rib fractures | 12 | M-M | 576 | 2.87 |
| 10 | M | 0 | E | Dystocia | Sepsis, anuric renal failure | 11 | Sev | 1812 | 8.21 |
| 11 | F | 48 | S | Bilateral laryngeal paralysis | Sepsis, congenital bilateral laryngeal paralysis | 12 | M-M | 156 | 5.17 |
| 12 | M | 6 | E | Dystocia | Sepsis | 11 | Sev | 230 | 5.96 |
| 13 | F | 12 | S | Dystocia, apnea, blue at birth | Sepsis | 14 | M-M | 150 | 9.64 |
| 14 | F | 12 | E | Premature placental separation | Sepsis | 15 | Sev | 168 | 1.86 |
| 15 | F | 24 | S | Unobserved foaling | No | 9 | M-M | 88 | 5.31 |
| 16 | F | 4 | S | Dystocia | No | 10 | M-M | 168 | 9.95 |
| 17 | F | 24 | S | No | No | 9 | Sev | 168 | 11.87 |
| 18 | M | 24 | S | Unobserved foaling | No | 15 | Sev | 186 | 2.74 |
| 19 | M | 16 | S | Dystocia | No | 9 | M-M | 274 | 7.18 |
| 20 | F | 0 | S | Dystocia (GA delivery) | Sepsis | 11 | M-M | 124 | 4.30 |
| 21 | M | 24 | S | No | Meconium impaction | 3 | M-M | 83 | 9.73 |
| 22 | F | 0 | E (economic) | Dystocia | No | 10 | Sev | 291 | 4.41 |
| 23 | F | 0 | S | No | Dysmaturity, high risk pregnancy | 6 | M-M | 124 | 4.30 |
| 24 | F | 0 | E (due to limbs) | Histology, placentitis | Contracture | n/a | M-M | n/a | n/a |
| 25 | F | 0 | S | No | No | 10 | Sev | 410 | 5.33 |
| 26 | M | 0 | E | No | Sepsis, gastrocnemius rupture, fetlock varus | 12 | Sev | 197 | 8.16 |
| 27 | F | 0 | S | No | Sepsis | 12 | Sev | 765 | 8.93 |
| 28 | M | 0 | S | Dystocia | No | 7 | M-M | 281 | 9.02 |
| 29 | M | 0 | S | Placentitis, rib fractures | Placentitis, rib fractures | 9 | M-M | 930 | 4.44 |
| 30 | M | 0 | S | Dystocia | Sick mare | 6 | M-M | 354 | 7.80 |
| 31 | M | 24 | S | Rib fracture | Sepsis, acute renal failure, rib fracture | 14 | Sev | 1528 | 2.98 |
| 32 | M | 0 | E (economic) | No | Severe meconium impaction | 2 | Sev | 183 | 6.18 |

Age = age at presentation;
M = male;
F = female;
E = euthanasia;
S = survival;
Sev = severe NMS;
M-M = mild-moderate NMS;
PMN = polymorphonuclear cell count.

TABLE 5

Case histories of sick control foal group (n = 12).

| Case | Gender | Age (h) | Outcome | Clinical Diagnosis | Sepsis Score | Creatinine (umol/l) | PMN ($\times 10^9$/l) |
|---|---|---|---|---|---|---|---|
| 1 | F | 0 | E (economic) | Prematurity, sepsis, intra-uterine growth restriction | 12 | 461 | 22.61 |
| 2 | F | 24 | E | Dysmature, sepsis, ARDS | 16 | 406 | 0.95 |
| 3 | F | 0 | E | Severe forelimb contracture | n/a | n/a | n/a |
| 4 | F | 0 | S | Dysmature, meconium impaction | 10 | 83 | 4.35 |
| 5 | F | 0 | S | Dystocia, assisted delivery, rib fractures | 4 | 243 | 6.64 |
| 6 | F | 0 | S | Dystocia, assisted delivery, angular limb deformities | 7 | 158 | 8.33 |
| 7 | M | 0 | S | Dysmature, meconium aspiration | 14 | 909 | 6.5 |
| 8 | M | 24 | E | Rib fractures, traumatic diaphragmatic hernia and colon rupture | 15 | 159 | 0.2 |
| 9 | F | 0 | S | Dysmature, sepsis | 12 | 181 | 9.48 |
| 10 | M | 0 | S | Bilateral forelimb contracture | 5 | 127 | 8.47 |
| 11 | F | 24 | S | Meconium impaction, urachal rent | 5 | 87 | 2.69 |
| 12 | M | 0 | S | Slightly weak | 1 | 118 | 6.37 |

Age = age at presentation;
M = male;
F = female;
E = euthanasia;
S = survival;
ARDS = acute respiratory distress syndrome;
PMN = polymorphonuclear cell count;
n/a = not available.

A third group of healthy control neonatal foals (n=10; 4 colts and 6 fillies) was recruited from the 2009 and 2010 foal crops at the Center for Equine Health, University of California, Davis.

Inclusion criteria for control foals included a term birth (>320 days gestation) with normal, uncomplicated delivery and physical examination.

All foals were less than 48 hours of age at enrollment into the study. No attempts were made to standardize treatments given to the foals during hospitalization. Outcome was recorded as survival to discharge. The study was approved by the University of California Institutional Animal Care and Use and Committee, and client consent was obtained prior to enrollment in the study.

Sample Collection and Analysis. Heparinized blood was collected from healthy control foals at 0, 24 and 48 h following birth. Samples were collected from NMS foals and other neonatal disease foals after initial stabilization and thereafter at the designated 24 and 48 h timepoints as appropriate. For foals presenting at birth, samples were collected within 2 h of parturition.

Whole blood was immediately centrifuged after collection and the plasma stored at −80° C. until analyzed. Plasma was analyzed by liquid chromatography mass spectrometry (LC-MS) utilizing on-line sample extraction by turbulent flow chromatography (TFC) and detection by select reaction monitoring (SRM) on a triple quadrupole mass spectrometer. Samples were diluted 2:1 with water fortified with four internal standards: D3-Testosterone, D3-Boldenone, D7-Androstenedione, and D3-Testosterone Sulphate. Analytes were separated by liquid chromatography using a Thermo TLX-2 TFC system with a Thermo Cyclone P extraction column and an ACE C18 analytical column. Analytes were introduced by electrospray ionization to a Thermo TSQ Vantage triple-quadrupole mass spectrometer operating in both negative and positive modes. Free steroid concentrations of 34 steroids were monitored in one analytical method over a 24 minute run time. Detection and quantitation was accomplished using 3 or more SRM transitions per compound for all compounds other than 17-hydroxy pregnenolone where Single Ion Monitoring (SIM) was utilized. This method was validated and the following assessed for each analyte: linearity, limit of detection, limit of quantitation, accuracy, precision, matrix effects, extraction recovery, and potential endogenous interferences. The following steroids were evaluated: pregnanes including progesterone, 17hydroxy-progesterone, 5α-dihydroprogesterone, pregenolone, allopregnanolone, and pregnanediol; androgens and estrogens including nandrolone sulphate, boldenone sulfate, 17-β estradiol sulphate, testosterone sulphate, 1,4-androstadien-3,17-one, testosterone glucoronide, 19-norandrostenedione, boldenone, androstenedione, nandrolone, estrone, testosterone, epinandrolone, epitestosterone, 6-α-hydroxyandrostenedione, nandrolone glucuronide, 17-β estradiol, 17-α estradiol, 19-norepiandrosterone, dehydroepiandrosterone (DHEA), DHEA-sulphate, 17-hydroxypregnenolone, 5-α dihydronandrolone, 5-α-estran-3-β-17-α diol, 5-α dihydrotestosterone, 19-nor-androsterone, 5-β dihydrotestosterone, estrone sulphate. These steroids were chosen due to convenience of a pre-existing, extensive steroid panel.

Data Analysis. Descriptive data are reported as median and ranges. Friedman tests were used for repeated measures analysis of steroid concentrations of healthy foals. Kruskal-Wallis tests were used for multiple group comparisons and Mann-Whitney tests for non-paired two group comparisons. Non-parametric tests were chosen based on the failure of the data to conform to normal distributions using a Kolmogorov and Smirnov test. Level of significance was set at $P<0.05$.

Results

On presentation, 19 NMS foals were graded as mild-moderate and 13 as severe. Altered states of consciousness of foals with NMS ranged from mildly obtunded to stuporous to comatose.

Several progestagens were detected in extremely low concentrations. Five steroids (both pregnanes and androgens) were consistently identified among foal samples; progesterone, pregnenolone, androstenedione, DHEA and epitestosterone. Healthy foals showed progressive, significant decreases in these steroids over the first 48 h of life (progesterone $P<0.0001$; pregnenolone $P<0.0001$; androstenedione $P=0.009$; DHEA $P=0.006$; epitestosterone $P=0.004$) (FIG. 2). There was no significant difference in healthy foal pregnane or androgen profiles between genders.

Compared to healthy foals, NMS foals showed elevated concentrations of androstenedione ($P=0.02$) and progesterone ($P=0.04$) at 0h (within 2 h of birth), androstenedione ($P=0.0002$), DHEA ($P=0.001$), epitestosterone ($P=0.0004$), progesterone ($P=0.0001$) and pregnenolone ($P=0.0007$) at 24 h of age, and androstenedione ($P=0.0008$), DHEA ($P=0.007$), progesterone ($P=0.0001$) and pregnenolone ($P=0.003$) at 48 h of age (FIG. 2, Table 6). Sick control foals also had significantly elevated concentrations of epitestosterone ($p=0.03$), progesterone ($P=0.001$) and pregnenolone ($P=0.05$) at 0h, androstenedione ($P=0.005$), DHEA ($P=0.003$), progesterone ($P=0.01$) and pregnenolone ($P=0.0009$) at 24 h and androstenedione ($P=0.004$), progesterone ($P=0.0004$) and pregnenolone ($P=0.0006$) at 48 h compared to healthy foals (FIG. 2, Table 6). Compared to sick control foals, NMS foals had significantly higher concentrations of epitestosterone at 0 and 24 h of age ($P=0.02$, $0.002$ respectively). In contrast, sick control foals had significantly higher progesterone concentrations than NMS foals at 0h ($P=0.01$). Whilst pregnane concentrations of sick control foals remained elevated above those of healthy foals, their progesterone and pregnenolone concentrations decreased significantly ($P=0.02$, $P=0.04$ respectively) over the 48 h. In contrast, steroid concentrations of NMS foals remained elevated and showed a trend of increasing concentration over time (FIG. 2).

TABLE 6

Median (range) serum steroid concentrations (ng/ml) in healthy, sick control and neonatal maladjustment syndrome (NMS) foals at 48 h of age.

| Steroid (ng/ml) | Healthy Control (n = 10) | Sick Control (n = 12) | NMS (n = 32) | P value (Kruskal Wallis) |
|---|---|---|---|---|
| Androstenedione | nd$^a$ (nd-0.51) | 1.15$^b$ (nd-7.65) | 6.56$^b$ (nd-57.34) | <0.0001 |
| DHEA | 7.68$^a$ (nd-117.90) | 101.14$^{a,b}$ (nd-1412.60) | 92.98$^b$ (nd-1,511.06) | 0.028 |

TABLE 6-continued

Median (range) serum steroid concentrations (ng/ml) in healthy, sick control and neonatal maladjustment syndrome (NMS) foals at 48 h of age.

| Steroid (ng/ml) | Healthy Control (n = 10) | Sick Control (n = 12) | NMS (n = 32) | P value (Kruskal Wallis) |
|---|---|---|---|---|
| Epitestosterone | nd (nd-0.15) | nd (nd-13.20) | 0.53 (nd-11.53) | 0.1 |
| Progesterone | nd$^a$ (nd-0.09) | 6.09$^b$ (1.97-14.28) | 14.22$^b$ (0.75-73.61) | <0.0001 |
| Pregnenolone | 103.76$^a$ (5.6-313.20) | 1119.40$^b$ (248.26-3,416.08) | 1922.08$^b$ (nd-15,917.33) | 0.001 |

DHEA = dehydroepiandrosterone;
nd = not detectable.
Groups with differing superscripts are significantly different (Mann-Whitney).

There was no significant difference in pregnane concentrations between mild-moderate and severely affected NMS foals. When considering all ill foals admitted to NICU, there was no significant difference in pregnane concentrations between survivors and non-survivors, septic and non-septic individuals and foals with and without a known history of hypoxia.

Discussion

The results of this study confirm that there are differences in the pregnane profiles of neonatal healthy foals, foals with NMS and foals with other clinical diagnoses. Pregnane concentrations of healthy neonatal foals declined rapidly, to essentially zero, within 48 h of birth in agreement with the study by Houghton et al. (1991). The foetal foal is subjected to high levels of progesterone and other progestagens in utero (Holtan, et al., (1991) *J Pediatr Psychol* 44, 517-528), which is deemed important in providing tonic inhibition of foetal CNS activity and damping movement to prevent maternal damage (Mellor, et al., (2005) *Brain Res Rev* 49, 455-471). Injections of progesterone or its metabolites into the ovine foetal circulation in late gestation reduce foetal electroencephalograph, electrocorticograph and electrooculograph activity, breathing movements and behavioural arousal, whilst inhibition of placental progesterone enhance these parameters (Crenshaw, et al., (1966) *Nature* 212, 842; Crossley, et al., (1997) *J. Reprod. Fertil. Dev.* 9, 767-773; Nicol, et al., (1997) *J Endocrinol* 152, 379-386; Nicol, et al., (2001) *Neurosci Letters* 306, 13-16). The loss of placentally derived precursors at birth and the switch to adrenal or other derived precursors causes this dramatic decline in pregnane concentrations shortly after birth in healthy neonates (Hirst, et al., (2006) *Neuroendocrinol* 84, 264-274).

Apart from epitestosterone concentrations of sick control foals, foals presenting ill to the Neonatal Intensive Care Unit (i.e. NMS and sick control foals) had higher concentrations of all measurable pregnanes than healthy controls within 2 h of birth. Pregnane concentrations of NMS foals remained elevated over the 48 h time period in contrast to those of sick control foals which had significantly lower progesterone and pregnenolone concentrations at 48 h compared to birth. Serial blood sampling with continued elevation or increasing pregnane concentrations over 48 h of age may therefore prove useful in aiding diagnosis and possibly prognosis of NMS; however further work is required to validate this possibility. These observations are consistent with the conclusion of a delayed, or interrupted, conversion from intra- to extra-uterine life in ill, neonatal foals, particularly those with NMS. This mechanism may be similar to that reported in foals of mares treated with the progestagen altrenogest which have a slower adaptation to the extra-uterine environment (Neuhauser, et al., (2008) *Exp Clin Endocrinol Diabetes* 116, 423-8.).

Pregnane profiles did not appear to differ between mild-moderate and severely affected foals although it is likely that a larger population needs to be sampled to detect such differences. Furthermore, the categorization used may have been inappropriate for finding such differences. In previous studies, pregnane concentrations decreased in foals with NMS as they displayed clinical improvement (Rossdale, et al., (1995) *Reprod Fertil Dev* 7, 567-575). This observation could not be validated by the current study as concentrations were only measured over the first 48 h of life. Pregnane concentrations were not significantly different between survivors and non-survivors in this study and, again, the short sampling period is likely to have precluded the ability to detect this finding. The effect of a known hypoxic episode on plasma pregnane profiles was examined due to the suggested aetiological role of hypoxia in NMS. Hypoxia did not appear to have an effect on pregnane concentrations; however it is impossible to accurately evaluate this criterion, particularly with regard intra-uterine hypoxia.

Differences in concentrations of pregnenolone and pregnanediol between sick and healthy foals have previously been described (Rossdale, et al., (1995) *Reprod Fertil Dev* 7, 567-575). Pregnanediol was not consistently measureable in the current foal population whereas the androgens, androstenedione and epitestosterone, have not previously been identified in foals with NMS (Rossdale, P. D. (2004) In: *Proceedings, 51st American Association of Equine Practitioners*, Denver, Colo. pp 75-126). It is likely that these analytes were simply not investigated in the analytical method originally developed (Houghton, et al., (1991) *J Reprod Fertil* 44, 609-617). LC-MS allows better differentiation of the individual steroids than can be achieved by radioimmunoassay (Rossdale, et al., (1997) *Equine Vet J* 24, S96-S99).

The cause of the increased plasma pregnane concentrations detected in ill neonatal foals cannot be elucidated from this study; however the authors propose that these concentrations occur as a result of persistence of foetal signals for the in utero state of being quiet and non-ambulatory. Certain pregnanes, such as progesterone, and their metabolites have neuromodulatory, anaesthetic and anxiolytic properties important for tonic inhibition of foetal CNS activity and damping foetal movement to prevent maternal damage (Mellor, et al., (2005) *Brain Res Rev* 49, 455-471). The receptors in the foetal brain are more sensitive to these pregnanes, compared with the receptors in the adult brain (Crossley, et al., (2000) *Neuropharmacology* 39, 1514-1522). Infusion of the neurosteroid pregnane allopregnanolone to healthy neonatal foals induces obtundation, lack of affinity for the mare, and decreased response to external stimuli (Madigan, et al., (2012) *Equine Vet J* 44:S41 109-112). These effects were short-lasting and associated with measurable concentrations of pregnanes (Madigan, et al., (2012) *Equine Vet J* 44:S41 109-112). This suggests that these steroids can cross the blood brain barrier and exert neuromodulatory effects, which at high concentrations may have a dampening effect in the CNS with resulting alterations in states of consciousness, altered behaviour, and responsiveness to stimuli, such as observed in NMS cases. The opposite may also apply; when certain pregnane concentrations are low, foals may be more alert, responsive to environmental stimuli, have affinity for the dam, and nurse. Specific enzymes may be inhibited in these foals and the roles of 5α-reductase, 3β-hydroxysteroid dehydrogenase and 3α-hydroxysteroid dehydrogenase need to be further evaluated. It has been suggested that the 5α-reduction step may be critical in determining the quantity of 5α-reduced pregnane metabolites either produced from progesterone within the foetal brain or derived from precursors entering the brain from the blood (Nguyen, et al., (2003) *Pediatr Res* 53, 956-964). The underlying cause of any possible abnormal adrenal function is also not known; it may reflect a state of dysmaturity in which the foal fails to transition to extra-uterine life or may reflect hypoxic injury to the HPA axis (Rossdale, et al., (1997) *Equine Vet J* 24, S96-S99). Another potential reason for persistence of foetal hormones is a failure of normal events of parturition which are an essential part of the signaling that the foal has transitioned to outside of the mare and the desire to rise and nurse can commence. The foetal state of sedation and limited movement in utero is critical to survival of the foal and mare and would require clear unequivocal signals of transition to outside of the uterus (birth). Events such as shorter times in the birth canal or altered deliveries might produce a failure of transition signals to allow foetal hormone reduction and the transition from the in utero foetal cortical status to extra-uterine behavioural status. Regulation of the neuroactive steroid content in the foetal ovine brain is independent of adrenal steroidogenesis and hypothalamic-pituitary factors (Nguyen, et al., (2004) *J Endocrinol* 182, 81-88) however, in the neonate, concentrations of some neurosteroids and their precursors in the peripheral circulation dramatically affect concentrations in the brain (Nguyen, et al., (2003) *Pediatr Res* 53, 956-964). Lastly, another possible mechanism would be the reversion to foetal cortical status when adverse post birth circumstances occur. The syndrome of reversion to foetal circulation is a well-known and accepted consequence of adverse birth and post birth events which cause the neonate to revert to mechanisms which regulated the cardiovascular system in utero.

It is also possible that the elevated pregnanes are acting in a neuroprotective role as has been reported in other species. Stress (hypoxia, endotoxin) in the neonatal period increases neurosteroid concentrations in the brain of newborn lambs (Hirst, et al., (2006) *Neuroendocrinol* 84, 264-274; Billiards, et al., (2002) *Pediatr Res* 52, 892-899), which is suggested to represent an endogenous protective mechanism. Similarly, acute, but not chronic, hypoxic stress during pregnancy increases foetal neurosteroid concentrations (Hirst, et al., (2006) *Neuroendocrinol* 84, 264-274). Indeed inhibition of neurosteroid synthesis increases asphyxia-induced brain injury in late gestation foetal sheep (Yawno, et al., (2007) *Neurosci.* 146, 1726-33).

Phenotypical characteristics of "maladjusted foals" may have more than one etiology (hypoxic/ischemic versus non-hypoxic/ischemic). The non-hypoxic foal is the one that lacks the normal transition from synthesis to inhibition of specific neurosteroids for readiness for birth (from foetal to neonatal neurosteroid profile). This may explain why some affected foals have a relatively fast recovery with no remaining long-term neurological deficits, and no apparent or known hypoxic events prior, during or shortly after birth.

Plasma concentrations of progestagens were measured in this study but ideally concentrations in brain tissue, which are known to be much higher than those in the peripheral circulation, would be measured. Neurosteroids and their precursors are known to cross the blood brain barrier (Wang, et al., (1997) *J Steroid Biochem Mol. Biol.* 62, 299-306) and are extremely potent such that small concentrations can have large local effects in neuronal tissue. Further, many steroids are metabolized to other compounds prior to exerting their effects.

In conclusion, specific alterations in pregnane profiles were detected between healthy control foals and ill, neonatal foals presenting to NICU. The anaesthetic and sedative properties of these pregnanes may account for the behavioural alterations seen in maladjusted and ill foals. These differences may reflect a delayed or interrupted transition from foetal to neonatal hypothalamic pituitary adrenocortical status. Repeated measurements of these pregnanes over time may be useful for distinguishing between foals with NMS and other neonatal disorders. Increased pregnane concentrations may cross the blood brain barrier and be responsible for some of the behavioural and neurological alterations observed in foals with NMS.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing and/or reversing a syndrome of reversion to fetal consciousness in a neonate mammal comprising:
   a) identifying a neonate mammal manifesting one or more clinical symptoms consistent with brain hypoxia;
   b) measuring the level of one or more pregnanes in a first biological sample from the neonate mammal;
   c) identifying and/or diagnosing the neonate mammal as suffering reversion to fetal consciousness when the level of one or more pregnanes in the first biological sample above a predetermined threshold level is measured; and
   d) upon measuring the level of one or more pregnanes above a predetermined threshold level and positively identifying and/or diagnosing the neonate mammal as suffering reversion to fetal consciousness, administering to the neonate an effective amount of a 5α reductase inhibitor and/or subjecting the neonate to squeezing along the mid-thorax; and
   e) measuring the level of the one or more pregnanes in a second or subsequent biological sample from the neonate mammal, wherein the syndrome of reversion to fetal consciousness is reduced and/or reversed when the level of the one or more pregnanes measured in the second or subsequent biological sample is below the predetermined threshold level.

2. The method of claim 1, wherein the neonate mammal is an equine.

3. The method of claim 1, wherein the neonate mammal is exhibiting symptoms of reversion to fetal consciousness.

4. The method of claim 1, wherein the one or more pregnanes measured comprise neurosteroidal activity.

5. The method of claim 1, wherein one or more pregnanes selected from the group consisting of progesterone, pregnenolone, 17OH progesterone and pregnanediol are measured.

6. The method of claim 1, wherein one or more pregnanes selected from the group consisting of progesterone and pregnenolone are measured.

7. The method of claim 1, wherein the predetermined threshold levels of the pregnane pregnenolone are above about 6000 ng/ml under 24 hours post birth, above about 550 ng/ml at 24-28 hours post birth and/or above about 315 ng/ml at or after 48 hours post birth.

8. The method of claim 1, wherein the predetermined threshold levels of the pregnane pregnenolone are above about 12,900 ng/ml under 24 hours post birth, above about 3470 ng/ml at 24-28 hours post birth and/or above about 3420 ng/ml at or after 48 hours post birth.

9. The method of claim 1, wherein the predetermined threshold levels of the pregnane progesterone are above about 10.5 ng/ml under 24 hours post birth, above about 0.8 ng/ml at 24-28 hours post birth and/or above about 0.1 ng/ml at or after 48 hours post birth.

10. The method of claim 1, wherein the predetermined threshold levels of the pregnane progesterone are above about 9.7 ng/ml at 24-28 hours post birth and/or above about 14.3 ng/ml at or after 48 hours post birth.

11. The method of claim 1, further comprising measuring androgen levels in the biological sample.

12. The method of claim 11, wherein one or more androgens are selected from the group consisting of androstenedione, dehydroepiandrosterone (DHEA), DHEA-sulphate and epitestosterone are measured.

13. The method of claim 1, wherein the biological sample is selected from the group consisting of blood, serum, plasma and urine.

14. The method of claim 1, wherein the level of the one or more preganes are measured at two or more time points.

15. The method of claim 1, wherein the 5α reductase inhibitor is selected from the group consisting of alfatradiol, dutasteride, finasteride, bexlosteride, episteride, izonsteride, lapisteride, turosteride, and analogs, salts and mixtures thereof.

16. The method of claim 1, wherein the applied pressure of the squeezing is maintained for at least 20 minutes.

17. The method of claim 1, wherein the one or more clinical symptoms consistent with brain hypoxia are selected from the group consisting of alterations in the state of consciousness, lack of affinity for the mother, failure to nurse, blindness, vocalization, wandering, paroxysmal activity and seizures.

18. The method of claim 1, wherein the neonate mammal is less than 120 hours post birth.

19. The method of claim 1, wherein the neonate mammal is less than 96 hours post birth.

20. The method of claim 1, wherein the neonate mammal is less than 72 hours post birth.

21. A method of reducing and/or reversing a syndrome of reversion to fetal consciousness in a neonate mammal comprising:
   a) identifying a neonate mammal manifesting one or more clinical symptoms consistent with brain hypoxia;
   b) receiving a first report providing the level of one or more pregnanes in a first biological sample from the neonate mammal;
   c) identifying and/or diagnosing the neonate mammal as suffering reversion to fetal consciousness when the level of one or more pregnanes in the first biological sample above a predetermined threshold level is measured;
   d) upon identifying the level of one or more pregnanes above a predetermined threshold level and positively identifying and/or diagnosing the neonate mammal as suffering reversion to fetal consciousness, administering to the neonate an effective amount of a 5α reductase inhibitor and/or subjecting the neonate to squeezing along the mid-thorax; and
   e) receiving a second or subsequent report providing the level of one or more preganes in a second biological sample from the neonate mammal, wherein the syndrome of reversion to fetal consciousness is reduced and/or reversed when the level of the one or more pregnanes provided in the second or subsequent report is below the predetermined threshold level.

22. The method of claim 21, wherein the neonate mammal is an equine.

23. The method of claim 21, wherein the neonate mammal is exhibiting symptoms of reversion to fetal consciousness.

24. The method of claim 21, wherein the one or more pregnanes measured comprise neurosteroidal activity.

25. The method of claim 21, wherein one or more pregnanes selected from the group consisting of progesterone, pregnenolone, 17OH progesterone and pregnanediol are measured.

26. The method of claim 21, wherein one or more pregnanes selected from the group consisting of progesterone and pregnenolone are measured.

27. The method of claim 21, wherein the predetermined threshold levels of the pregnane pregnenolone are above about 6000 ng/ml under 24 hours post birth, above about 550 ng/ml at 24-28 hours post birth and/or above about 315 ng/ml at or after 48 hours post birth.

28. The method of claim 21, wherein the predetermined threshold levels of the pregnane pregnenolone are above about 12,900 ng/ml under 24 hours post birth, above about 3470 ng/ml at 24-28 hours post birth and/or above about 3420 ng/ml at or after 48 hours post birth.

29. The method of claim 21, wherein the predetermined threshold levels of the pregnane progesterone are above about 10.5 ng/ml under 24 hours post birth, above about 0.8 ng/ml at 24-28 hours post birth and/or above about 0.1 ng/ml at or after 48 hours post birth.

30. The method of claim 21, wherein the predetermined threshold levels of the pregnane progesterone are above about 9.7 ng/ml at 24-28 hours post birth and/or above about 14.3 ng/ml at or after 48 hours post birth.

31. The method of claim 21, further comprising measuring androgen levels in the biological sample.

32. The method of claim 31, wherein one or more androgens are selected from the group consisting of androstenedione, dehydroepiandrosterone (DHEA), DHEA-sulphate and epitestosterone are measured.

33. The method of claim 21, wherein the biological sample is selected from the group consisting of blood, serum, plasma and urine.

34. The method of claim 21, wherein the level of the one or more pregnanes are measured at two or more time points.

35. The method of claim 21, wherein the one or more clinical symptoms consistent with brain hypoxia are selected from the group consisting of alterations in the state of consciousness, lack of affinity for the mother, failure to nurse, blindness, vocalization, wandering, paroxysmal activity and seizures.

36. The method of claim 21, wherein the neonate mammal is less than 120 hours post birth.

37. The method of claim 21, wherein the neonate mammal is less than 96 hours post birth.

38. The method of claim 21, wherein the neonate mammal is less than 72 hours post birth.

* * * * *